(12) United States Patent
Gomez Acevedo

(10) Patent No.: US 12,127,806 B1
(45) Date of Patent: Oct. 29, 2024

(54) COMPUTER-ASSISTED SURGICAL ROBOTIC ABLATION

(71) Applicant: Hector Humberto Gomez Acevedo, Mexico City (MX)

(72) Inventor: Hector Humberto Gomez Acevedo, Mexico City (MX)

( * ) Notice: Subject to any disclaimer, the term of this patent is extended or adjusted under 35 U.S.C. 154(b) by 620 days.

(21) Appl. No.: 17/243,166

(22) Filed: Apr. 28, 2021

Related U.S. Application Data

(60) Provisional application No. 63/173,920, filed on Apr. 12, 2021.

(51) Int. Cl.
| | |
|---|---|
| *A61B 34/30* | (2016.01) |
| *A61B 34/00* | (2016.01) |
| *A61B 34/10* | (2016.01) |
| *A61B 90/00* | (2016.01) |
| *A61B 90/30* | (2016.01) |

(52) U.S. Cl.
CPC .............. *A61B 34/70* (2016.02); *A61B 34/10* (2016.02); *A61B 34/30* (2016.02); *A61B 90/37* (2016.02); *A61B 2090/306* (2016.02); *A61B 2090/374* (2016.02); *A61B 2090/3762* (2016.02); *A61B 2090/378* (2016.02); *A61B 2562/0271* (2013.01)

(58) Field of Classification Search
CPC ......... A61B 34/10; A61B 34/30; A61B 34/70; A61B 90/37; A61B 2090/306; A61B 2090/374; A61B 2090/378; A61B 2090/3762; A61B 19/201; A61B 19/203; A61B 19/5244
See application file for complete search history.

(56) References Cited

U.S. PATENT DOCUMENTS

| | | | |
|---|---|---|---|
| 2020/0078113 A1* | 3/2020 | Sawhney | A61B 34/20 |
| 2020/0100830 A1* | 4/2020 | Henderson | G16H 40/63 |

* cited by examiner

*Primary Examiner* — Vi X Nguyen
(74) *Attorney, Agent, or Firm* — Michael D. Eisenberg

(57) ABSTRACT

An example system may include a processor of a computer node operatively connected to a computer-guided robotic arm configured to manipulate a medical instrument attachable to the robotic arm and comprising a laser beam emitter located at a distal end of the medical instrument; a memory on which are stored machine readable instructions that when executed by the processor, cause the processor to: cause the robotic arm to perform movements comprising extend, retreat or spin, acquire imaging data of a patient concurrent to the movements of the robotic arm, and configure emission parameters of the laser beam based on the imaging data.

6 Claims, 15 Drawing Sheets

COMPUTER-ASSISTED SURGICAL ROBOTIC ABLATION

TECHNICAL FIELD

This application generally relates to surgical robotics, and more particularly, to computer-assisted robotic ablation using laser.

BACKGROUND

Currently, various implementations of robotic arms are used for medical procedures. The robotic arms are used to make holes and place screws on the spinal vertebras. There are also robotic arms/hands that replicate the surgeon's movements in real-time for surgery, employing tongs, scissors, electric fulguration and lasers. The lasers are used for ablation of human tissue, such as the laser ablation of prostates using an endoscope with a laser beam emitter through the urethra.

However, lasers are not used in combination with robotics. However, use of lasers with robotic arms can enhance a capability of inserting a laser within a needle inside a patient's body to ablate cellular tissue in a precise pre-programmed shape that contains the tumor without damaging normal tissue during a surgical approach and resection. Use of lasers in stereotactic radio-surgery (X-Rays or Gamma Radiation) which relies on the amount of ionizing radiation that human body may receive (usually limiting the Radio-surgery to small tumors), may be improved by use of lasers. Since the laser ablates only a few millimeters per beam shot, much bigger tumors may be treated with this pre-programmed ablation volumetric shape, leaving adjacent normal tissue unharmed.

Accordingly, a system and method for computer-assisted surgical robotic ablation with lasers are desired.

BRIEF SUMMARY OF INVENTION

One example embodiment provides a processor of a computer node operatively connected to a computer-guided robotic arm configured to manipulate a medical instrument attachable to the robotic arm and comprising a laser beam emitter located at a distal end of the medical instrument; a memory on which are stored machine readable instructions that when executed by the processor, cause the processor to: cause the robotic arm to perform movements comprising extend, retreat or spin, acquire imaging data of a patient concurrent to the movements of the robotic arm, and configure emission parameters of the laser beam based on the imaging data.

In a variant, the emission parameters of the laser beam comprising direction, intensity and duration of the emission of the laser beam configured to destroy pre-defined shape and volume of cellular tissue of a body of a patient.

In another variant, the instructions further cause the processor to control pulses of the laser beam and intensity of the pulses.

In yet another variant, the instructions further cause the processor to acquire the imaging data comprising MRI data, CT scan data or ultrasound data.

In a further variant, the instructions further cause the processor to auto-regulate frequency and intensity of laser shoots based on a temperature sensor data acquired throughout a laser conducting optic fiber.

In yet a further variant, the instructions further cause the processor to acquire real-time data from a plurality of feedback sensors and from at least one infrared camera for positioning of the robotic arm.

The instructions may further cause the processor to coordinate the movements of the robotic arm with movements of other robotic arms using the real-time data from the plurality of feedback sensors and from the at least one infrared camera.

Another example embodiment provides a method that includes one or more of causing, by a computer node operatively connected to a computer-guided robotic arm, the robotic arm to perform movements comprising extend, retreat or spin; acquiring, by the computer node, imaging data of a patient concurrent to the movements of the robotic arm; and configuring, by the computer node, emission parameters of a laser beam produced by an emitter located at a distal end of the medical instrument attached to the robotic arm based on the imaging data.

In a variant, the emission parameters of the laser beam comprising direction, intensity and duration of the emission of the laser beam configured to destroy pre-defined shape and volume of cellular tissue of a body of a patient.

In another variant, the method further comprises controlling pulses of the laser beam and intensity of the pulses.

In yet another variant, the method further comprises acquiring the imaging data comprising MRI data, CT scan data or ultrasound data.

In a further variant, the method further comprises auto-regulating frequency and intensity of laser shoots using data acquired throughout a laser conducting optic fiber by a temperature sensor.

In yet a further variant, the method further comprises, acquiring real-time data from a plurality of feedback sensors and from at least one infrared camera for positioning of the robotic arm.

The method may further comprise coordinating the movements of the robotic arm with movements of other robotic arms using the real-time data acquired from the plurality of feedback sensors and from the at least one infrared camera.

A further example embodiment provides a non-transitory computer readable medium comprising instructions, that when read by a processor, cause the processor to perform one or more of causing a robotic arm operatively connected to the computer node to perform movements comprising extend, retreat or spin; acquiring imaging data of a patient concurrent to the movements of the robotic arm; and configuring emission parameters of a laser beam produced by an emitter located at a distal end of the medical instrument attached to the robotic arm based on the imaging data.

In a variant, the non-transitory computer readable medium further comprises instructions, that when read by the processor, cause the processor to control pulses of the laser beam and intensity of the pulses.

In a variant, the non-transitory computer readable medium further comprises instructions, that when read by the processor, cause the processor to acquire the imaging data comprising MRI data, CT scan data or ultrasound data.

In a variant, the non-transitory computer readable medium further comprises instructions, that when read by the processor, cause the processor to auto-regulate frequency and intensity of laser shoots based on a temperature sensor data acquired throughout a laser conducting optic fiber.

In a variant, the non-transitory computer readable medium further comprises instructions, that when read by the processor, cause the processor to auto-regulate frequency and intensity of laser shoots using data acquired throughout a laser conducting optic fiber by a temperature sensor.

The non-transitory computer readable medium may further comprise instructions, that when read by the processor, cause the processor to acquire real-time data acquired from a plurality of feedback sensors and from at least one infrared camera for positioning of the computer-guided robotic arm.

DETAILED DESCRIPTION OF THE EMBODIMENTS OF THE INVENTION

Figure 1:
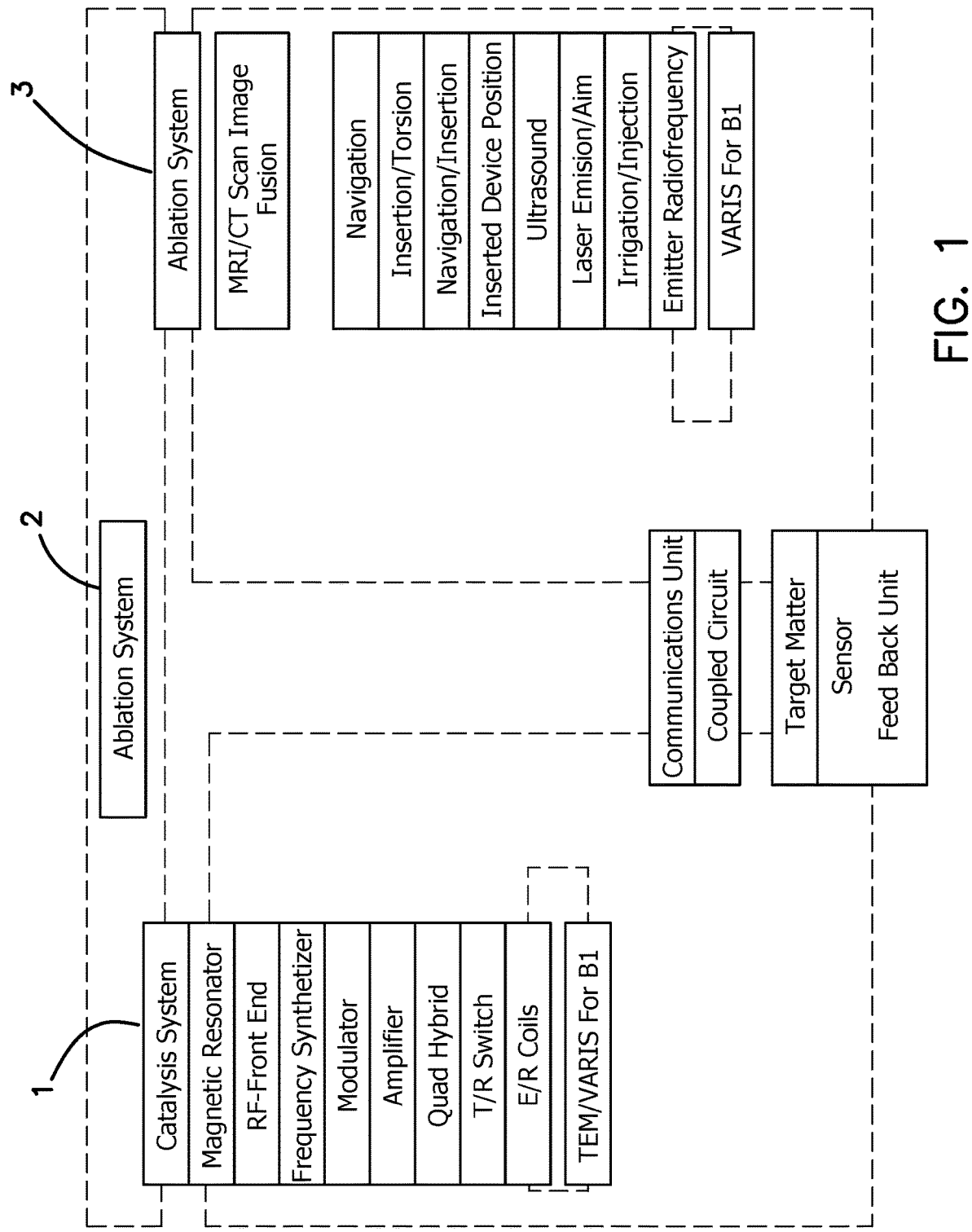
FIG. 1 illustrates a novel Electromagnetic Resonance Catalysis-Ablation System in a functional schematic approach, according to example embodiments.

It will be readily understood that the instant components, as generally described and illustrated in the figures herein, may be arranged and designed in a wide variety of different configurations. Thus, the following detailed description of the embodiments of at least one of a method, apparatus, non-transitory computer readable medium and system, as represented in the attached figures, is not intended to limit the scope of the application as claimed but is merely representative of selected embodiments.

The instant features, structures, or characteristics as described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" may have been used in the description of embodiments, the application may be applied to many types of network data, such as, packet, frame, datagram, etc. The term "message" also includes packet, frame, datagram, and any equivalents thereof. Furthermore, while certain types of messages and signaling may be depicted in exemplary embodiments they are not limited to a certain type of message, and the application is not limited to a certain type of signaling.

The exemplary embodiment may provide a system and method comprising a digitally-guided surgical robotic instrument that inserts in the living tissue of individuals, a carrier in the shape of the tip of a hollow needle or catheter in order to produce a change on such living tissue, such as ablation with a laser, cauterization with an electrode, heating or scanning with an ultrasound transducer or to radiate with an emitter antenna or radioactive material, tissue retrieval with biopsy tongs. The main advantage of this instrument is that the position, orientation and approach trajectory and interaction with the tissue is computer controlled and navigated with anatomic images of the patient such as Magnetic Resonance Image (MRI), CT scan and ultrasound, allowing precise instruments interaction with the desired tissue's location shape and volume only mostly avoiding undesired damage to surrounding cells.

Laser ablation or photo-ablation is the process of removing material from a solid (or occasionally liquid) surface by irradiating it with a laser beam. At low laser flux, the material is heated by the absorbed laser energy and evaporates or sublimates. At high laser flux, the material is typically converted to plasma. Usually, laser ablation refers to removing material with a pulsed laser, but it is possible to ablate material with a continuous wave laser beam if the laser intensity is high enough. Excimer lasers of deep ultra-violet light are mainly used in photo-ablation. The wavelength of laser used in photo-ablation is approximately 200 nm.

Figure 2:
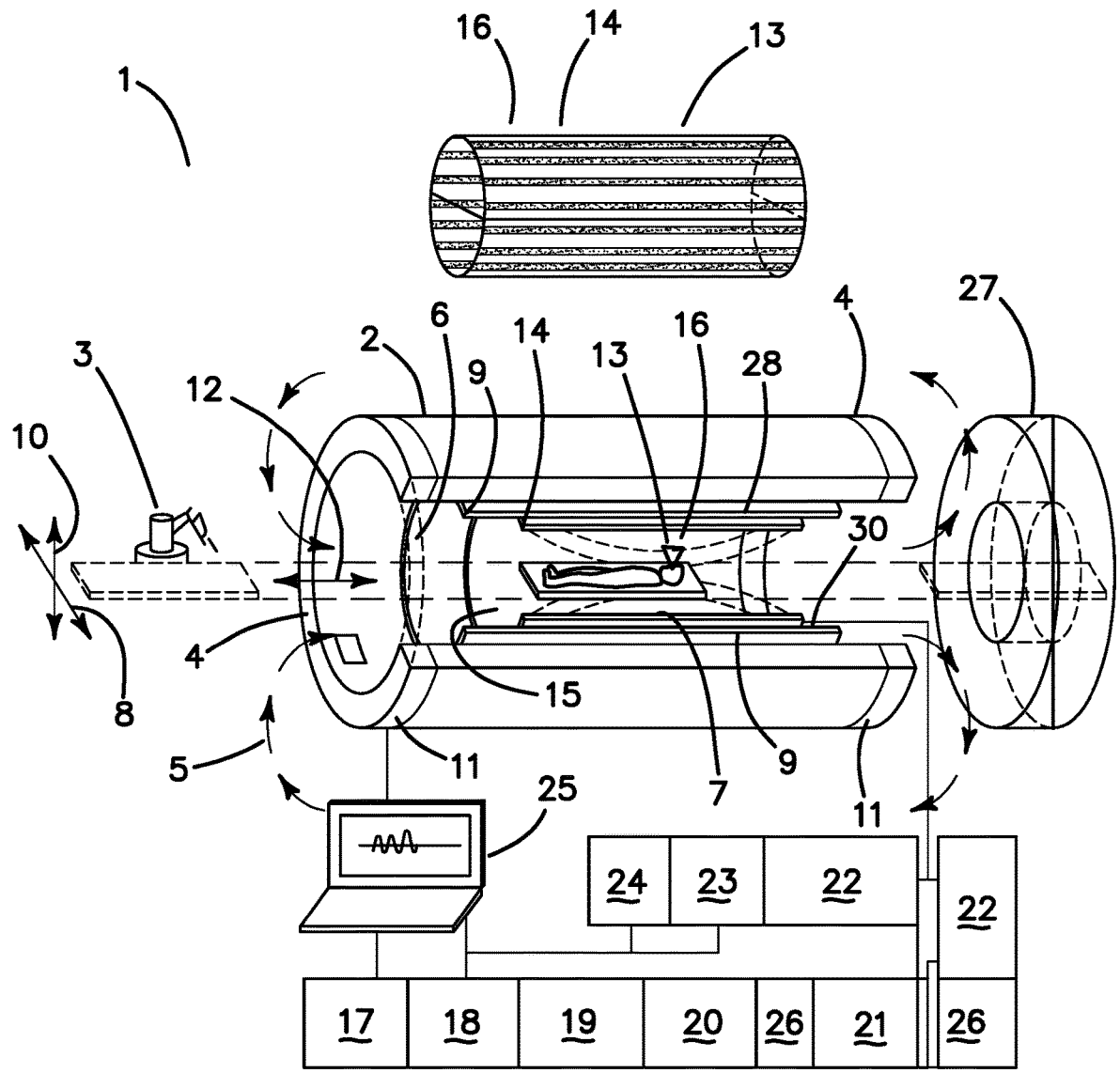
FIG. 2. illustrates the novel Electromagnetic Resonance Catalysis-Ablation System including the Catalysis and the Ablation systems, according to example embodiments.
Figure 3:
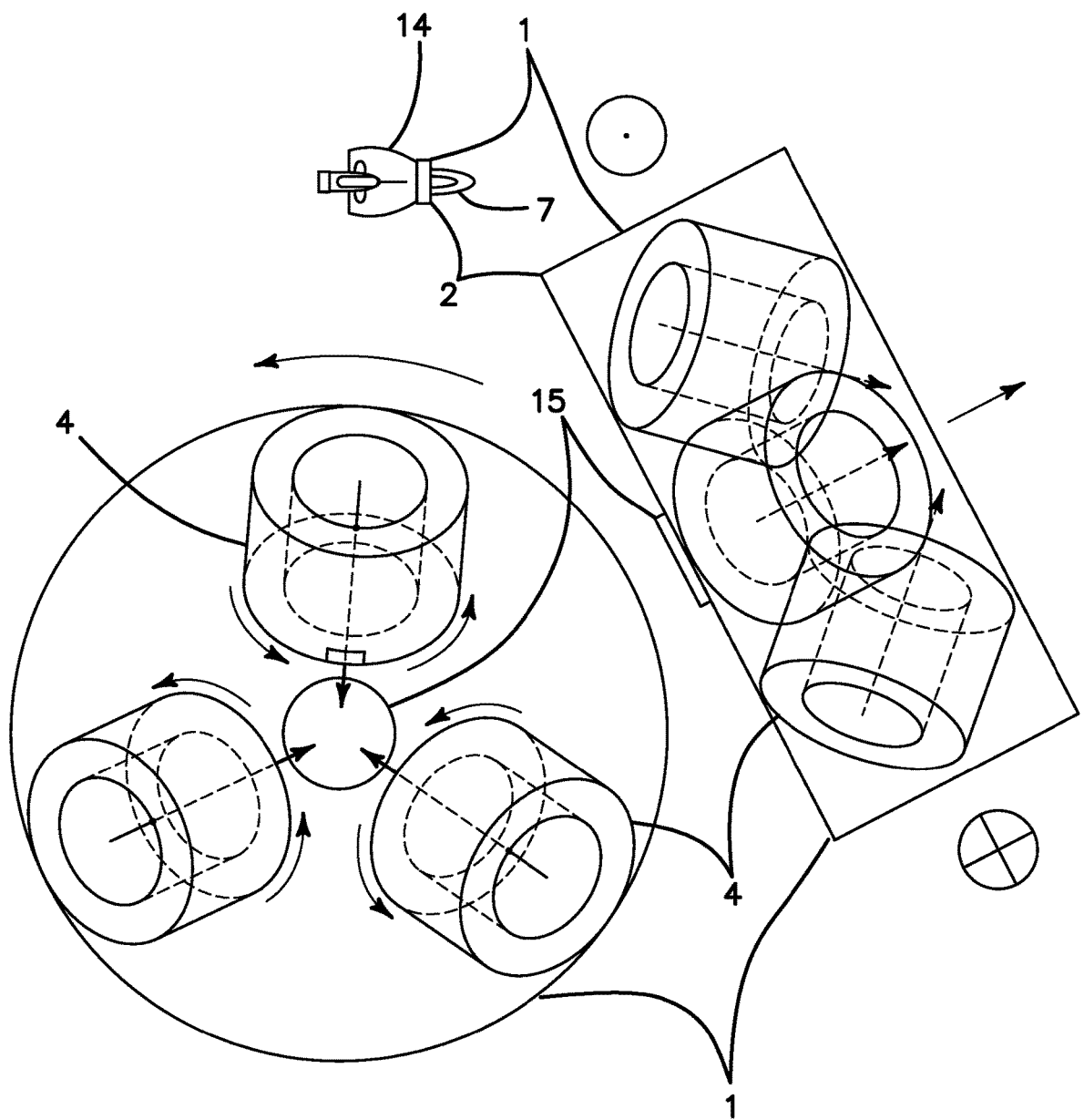
FIG. 3 illustrates an embodiment of the Catalysis System applied to engines, according to example embodiments.

FIG. 1. illustrates a novel Electromagnetic Resonance Catalysis-Ablation System 1 in a functional schematic approach. The Catalysis System 2 selectively facilitates desired chemical reactions on molecules of interest using resonant electromagnetic energy. The Ablation System 3 destroys, using an inserted laser, under computer control, undesired material of any shape, preserving surrounding material and tissues. Thus, the novelty of this Ablation System includes a navigated computer-controlled inserted laser with variable aim aided by exchangeable radiofrequency, ultrasound and irrigation sub systems. Both systems 2 and 3 designed to work together as an advanced medical tool are shown in FIGS. 1, 2, and 3. As an example of synergized interaction and given that the Catalysis System 2 uses Magnetic Resonance Imaging (MRI), the MRI/CT Scan images obtained from an immobile patient (usually under anesthesia) in a particular position may be used for immediate insertion of the deliverer instrument used as a main tool for the Ablation System 3. Thus, further positioning of the patient with necessary fiducially array may be avoided. Another example of synergic interaction appears when the Catalysis System enhances medical drug interaction with matter to be catalyzed, such a tumor, while using the Ablation System to inject chemotherapeutic drugs directly into the tumor.

FIG. 2. illustrates the novel Electromagnetic Resonance Catalysis-Ablation System including the Catalysis and the Ablation systems.

Both systems 2 and 3 are designed to work in a synergic manner on the same apparatus 1. The catalysis system 2 and the ablation system 3 are designed, when needed, to also work in an independent manner from each other. The Catalysis System 2 includes at least two coil systems, where the first coil system 4 produces a strong magnetic field known as B0 5 created by the interaction of three pairs of coils, being the first couple 6 located lateral (at each side) to the target matter 7 (i.e., the matter of interest to be catalyzed), parallel to each other and perpendicular to the X axis 8. The second couple of coils 9 are located below and upside of the target matter and are also parallel to each other and perpendicular to the y axis 10. The third couple of coils 11 is located at each end of the target matter also parallel to each other and perpendicular to the z axis 12. The strong magnetic field B0 5 of approximately 0.5 to 35 Tesla or more when possible may affect the orientation of the spin axis of protons of the target matter 7 that is located on the strong magnetic field B0 5. The second system of coils 13 includes an array of emitter/receiver antennas 14 that produces far-field electromagnetic radiation B1 15 from different antennas 14 (radiation sources) and in a synchronized manner into the target matter 7. The MRI involves the absorption and emission of energy by nuclei at a specific resonant (Larmor's) frequency.

The Larmor's frequency scales directly with main magnetic field strength B0 5, and for clinical MRI, it lies in the range of tens to hundreds of MHz. These frequencies are part of the electromagnetic spectrum commonly used for radio transmission. A time-varying radiofrequency (RF) field, commonly referred to as B1 15, must be first transmitted into the spin system near the Larmor's frequency. In addition to having specific frequency, the B1 15 field must also be applied perpendicular to the main magnetic field B0 5. The B1 15 field is produced by driving electrical currents through specialized RF-transmit coils such as TAM 16. These coils are located either within the inner walls of the scanner or as free-standing devices connected by cables placed on or near the patient. A sophisticated electronic "RF-front end" 17 is responsible for generating, shaping, and amplifying the electrical currents required to produce the B1 field 15. The basic components in this RF-transmit chain 17 are: Frequency Synthesizer (18)→Modulator (19) →Amplifier (20)→Quad Hybrid (21)→T/R Switch (22) →Coil (13). So, the Frequency synthesizer 18 component produces a continuous sinusoidal carrier wave at (or near) the Larmor's resonant frequency. Driven by a quartz crystal, the synthesizer 18 utilizes a numerically controlled oscillator (NCO) 23 monitored by a phase-locked loop (PLL) 24 to maintain precise digital control over frequency and phase. The output from the synthesizer 18 will be sent two places simultaneously: 1) further down the RF-transmitter chain 17 to the pulse modulator 19 for shaping; and 2) into the RF-receiver chain 25 where it will be used as a reference for demodulating/decoding the MR signal. The Pulse modulator 19 is employed given that usually the B1 15 fields used to catalyze molecules are not transmitted as continuous waves, but in short (1-5 ms) bursts, called RF-pulses. The continuous carrier wave from the frequency synthesizer 18 must, therefore, be "chopped up" into small pieces and these pieces appropriately "shaped" into pulses as dictated by the particular application. The contours of each RF-pulse are specified using 100-200 data points, and are therefore of low-frequency (measured in kHz). The pulse-shape data is used to modulate the carrier wave so that the resultant output is a mixture of frequencies centered around the carrier. The newly fashioned RF-pulse next passes through a high-power amplifier 20 that generates the large currents necessary to drive the RF-coils 13. The amplifiers used in modern MR systems typically produce peak power in the range of 10-30 kW resulting in maximum transmitted B1 15 fields in the order of 10-50 µT. The gain of the power amplifiers 20 is adjusted by an active circuit element called the transmit attenuator 26. By changing the degree of RF attenuation (or alternatively, its gain/amplification) the flip angle of the RF pulse is adjusted. The terminology and measurement units differ, being variously referred to as transmission attenuation, transmit gain, RF gain, reference amplitude, RF level, or RF drive scale. Regardless of name, monitoring RF gain/attenuation is an important part of regular quality control to insure the scanner transmitter chain elements 17, 25 are working properly. The output of the power amplifier is typically split into two equal parts by means of a quadrature hybrid coupler device 21. The resultant outputs are 90° out of phase with one another and are used to feed the two ports of the quadrature transmit 21 coil. The two outputs of the coupler are known as I and Q, standing for "in phase" and "quadrature" respectively. The currents in the I and Q outputs of the coupler is now headed for the RF-transmitter coils 13. As scanners may have several possible transmitter coils 13, electronic switching circuitry 22 is necessary to make sure that current is delivered to the proper coil at the proper time. Additionally, sometimes the same coils 13 are used to both transmit B1 15 and receive the MR signal. For these coils a special Transmission/Reception switch 22 is required to isolate the two functions and make sure the powerful electric currents used for transmission do not go into and burn up the sensitive receiver circuitry. Note that although RF-coils 13 transmit electromagnetic radiation in the range of "radio waves," the emitted MR signal is not itself a conventional radio wave given that coherent spontaneous emission (radio waves) is not responsible for the vast majority of the Magnetic Resonance signal induced in an open-circuit receiving coil.

Rather, most Magnetic Resonance Image is a near-field phenomenon described accurately and classically by Faraday's Law. Given that the latter is derived from Coulomb's Law with the aid of relativity, it seems reasonable to accept the concept that coherent virtual photons provide the near electric field that gives an electromotive force and to associate them with near angular momentum. It is correct to consider radio frequencies, but probably not radio waves. As shown on FIG. 2, the embodiment for this array of antennas 13 is the transverse electromagnetic (TEM) resonator 16 instead of a more commonly used bird cage antenna shape. The TEM resonator 16 differs from a birdcage coil antenna since the TEM 16 coil typically uses foil micro strips (microcircuits) instead of rods affixed to the inner surface of a no conducting cylinder, and the TEM 16, on the outer surface of the cylinder, comprises a slotted thin metallic shield 27. Besides, the Catalysis-Ablation System 2 may also include a CT Scan 28 in order to fusion the images from the CT Scan 28 with the ones from the MRI 29 to obtain more precise and less distorted anatomical images to be used by the navigation part of the Ablation System 3. According to one embodiment, the micro-strips of the TEM resonator 16 are used to produce multiple sources of synchronized electromagnetic radiation B1 15 that best affects the target molecules 7 according to atomic and molecular resonant frequencies and Larmor's resonant frequencies. Given that the micro-strips of the TEM 16 emitter antenna usually work specifically only for already set frequencies, it becomes necessary to use an array of antennas 13 that may emit electromagnetic waves at variable frequencies. Although the variable frequencies emitter antennas for the TEM 16 might be commercially available, said the example Catalysis System 2 includes a Variable Inductance Solenoid as a novel component of the array of antennas 13 and it will be further discussed herein.

With regard to the Electromagnetic Catalyzer System 2, given that the strong magnetic field B0 5 is affecting the spin of the electrons, the TEM 16 configuration emitter antenna produces far-field electromagnetic radiation in the frequency of radio waves to micro-waves. The specific way this innovation expects to alter matter, relies on the torsion and rotation of the molecules. The torsion created by electromagnetic energy on the microwave and/or radio frequencies affecting the molecules is given as a function of its dipolar charge and also produces heat. However, this present innovation 1 is implemented by change in orientation of the spin axis of protons provided by the magnetic B0 5, plus the far-field electromagnetic radiation B1 15 that produces molecular rotation and torsion, enhancing molecular instability. The molecular increased instability is produced by the synergic effect of B0 5 and B1 15. If needed, accordingly to the kind of chemical reaction expected, an electromagnetic cage 30 is also present as a part of the transverse electromagnetic resonator 16. Thus, bouncing back the electromagnetic radiation from the walls of the cage 30 millions of times through the target matter 7 occurs in a similar way as what happens inside of a microwave oven. A similar but not equal effect is achieved by the Magnetic Resonance Imaging (MRI) 29 apparatus with a difference that the MRI has the Larmor's resonant frequency tuned to the Hydrogen atoms of the water molecules (H2O). The MRI 29 only affects the spinning angle of the electrons by providing extra magnetic energy, generating photonic radiation when the electrons return to a lower energy level. The near-field photonic radiation is sensed by the TEM 16 receiving antennas, generating images accordingly to water and hydrogen variation amongst tissues. The Catalysis System 2 has the advantage over the MRI 29, because different molecules than water and different atoms than Hydrogen may now be targeted in order to produce a resonant effect. Another advantage over the standard MRI 29 lies in the fact that changes on B0 5 intensity produces a change on Larmor's resonant frequency.

Thus, different Larmor's frequencies from same targets may be elicited accordingly to which frequency best produces molecular instability, being the targeting far-field electromagnetic radiation frequencies emitted by the emitter antennas 13 of the variable field B1 15. So the difference with the instability that produces heat (where it affects all present molecules), relies on the so called Magneto-radiation Resonance Catalysis System and Method 2. Such effect is based on the fact that specific atoms and molecules may be targeted (using Larmor's frequencies) without overheating the targeted matter 7. Customized instability may now be particularly enhanced accordingly to the Larmor's resonant frequency of each chosen chemical element and/or molecule, particularly when the molecules are also being stimulated by added up resonant far-field electromagnetic waves. (The called resonant electromagnetic effect also produces large electron jumps on matter that have not been yet well understood on modern physics). Given that specific molecules may now be forced to become more instable, the selective molecular targeting for catalysis on chemistry and biochemistry is an advantage provided by this innovation 1. As an example of expected applications of this novel technology, without departing from the scope of the innovation, a viral spike (As the one from the new corona virus (COVID-19)) is made of nucleotides and sugars (glucose) that the virus employs to recognize and attach to cellular human membranes. It is known that the spike is fragile and becomes unstable and breaks down under laboratory observation. For instance at 40 degrees Celsius and with a pH of 8. Thus, magneto-radiation catalysis by the targeting of the spikes or other molecules of other infectious agents is expected. In order to change the Larmor's frequency, when needed and given that the frequency changes under a variable strong magnetic field, the magneto-radiation catalysis may also be performed under the effects of a fluctuating strong magnetic field (B0 variable). Given that this technology (magneto-radiation catalysis) enhances chemical reactions, reactants in the form of chemical compounds may and should also be present for better results. Note that given that this novel technology provides the possibility of interaction with complex proteins by catalyzing specific types and sub-types of biochemical compounds it may be possible to produce even genetic therapy. For instance, if histones are catalyzed (the proteins that repair our DNA) and are made more prone to be catalyzed (more prone for the chemical reaction the molecule performs itself or it might also facilitate, behaving as an enzyme), the diseases related to imperfect genetic expression might now be treated using this kind of DNA repair (e.g., Cancer, Alzhaimer, Aging, etc.).

Note that according to one embodiment, it is possible to use the Larmor's resonant frequencies of different elements to achieve desired reactions. One of the applications is to retrieve calcium and lipids from the lumen of an artery. For that matter, an animal or a human may be placed under the influence of both the magnetic fields (5, 15) using the Larmor's resonant frequency of Calcium (instead of Hydrogen) to enhance Calcium release from the inner wall of the specimen's arteries. Note that during the catalysis of the desired molecules additional energy such as ultrasound or laser may be also applied to the desired target matter 7 in order to better remove Calcium from the inner wall. Some atoms are more prone to be affected by electromagnetic radiation accordingly to their atomic valence.

Note that the Catalysis System described technology may also be employed on propulsion engines, plasma engines and antimatter engines in order to improve performance. While the plasma and antimatter engines already use electromagnetic radiation end magnetic fields to make the engines work, the exact difference with proposed technology is the tuning of the electromagnetic radiation B1 on the Larmor's frequency of the mater used as propellant under the influence of a strong magnetic field B0. The catalysis enhances energy release in order to improve thrust.

FIG. 3 illustrates an embodiment of the Catalysis System applied to engines, where the target matter is the propellant (i.e., chemical exothermic reaction compounds, plasma, antimatter, etc.) expelled through multiple solenoids that produce independent variable strong magnetic fields B0 5 combined with the electromagnetic waves B1 15 emitter antennas 14 in order to produce a enhance positive burning thrust resonant effect while concurring on a resonant thrust chamber. Note that the solenoids 4 include three hollow ferric core solenoids 4 that aim to a central resonant chamber given that the propellant (now catalyzed material 7) passing through each the three solenoids 4 concurs on the resonant chamber. The preferred embodiment comprises electromagnetic waves emitter antennas 14 on the vortex of the thrust resonant chamber. Thus, the strong magnetic fields B0 5 are produced in order to generate thrust resonant magnetic effect on the concurrent ionized propelling material 7 coming through the three solenoids.

Figure 4:
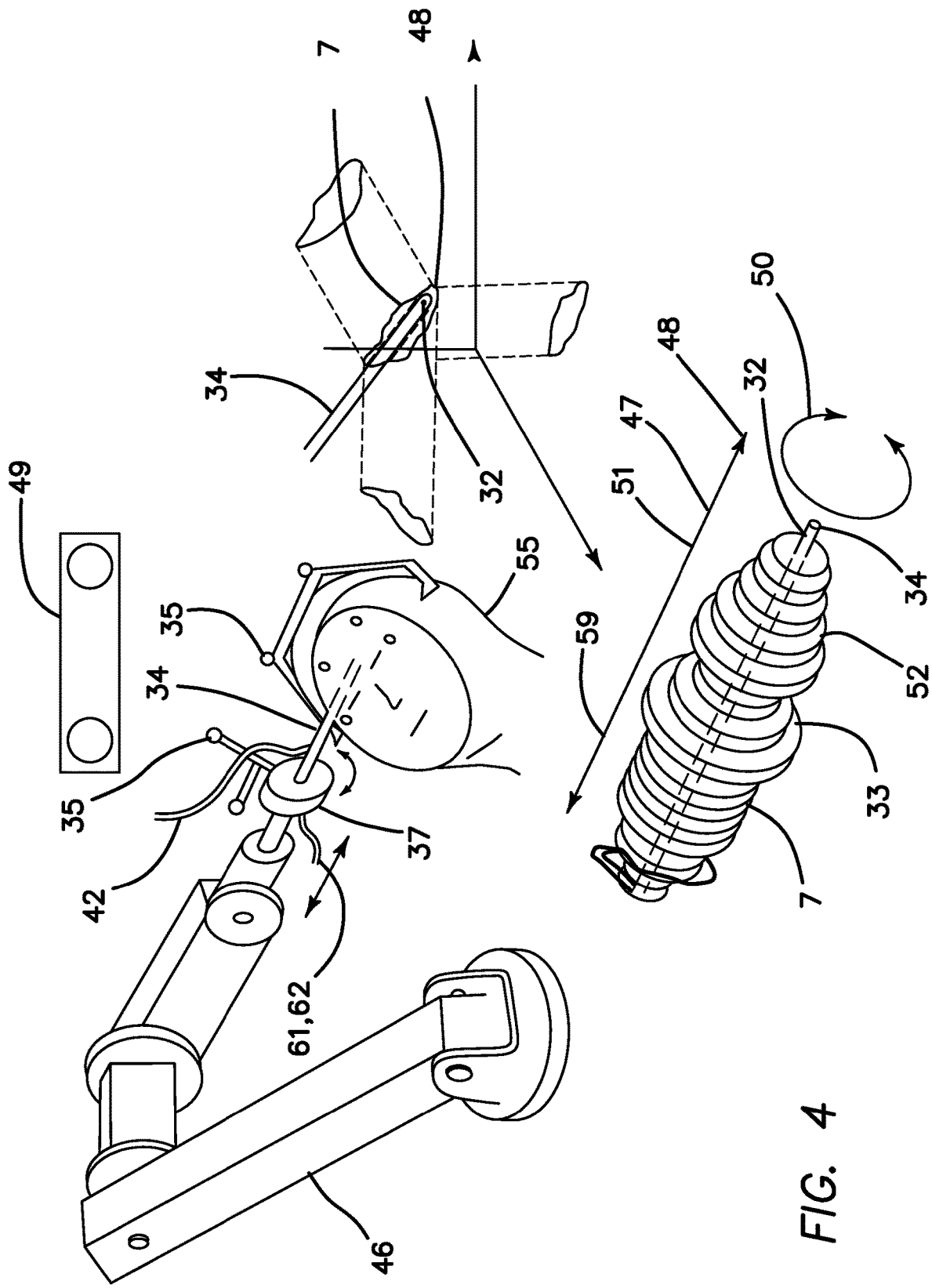
FIG. 4 illustrates an image-assisted digitally guided surgical robotic instrument also known as ablation system, according to example embodiments.

FIG. 4 shows an image-digitally guided surgical robotic instrument also known as an Ablation System. This system includes a digitally-guided surgical robotic instrument configured to be inserted into a living tissue of a patient, a carrier 34 in the shape of the tip of a hollow needle or catheter configured to produce a change on such living tissue, such as ablation with a laser, cauterization with an electrode, heating or scanning with an ultrasound transducer or to radiate with an emitter antenna or radioactive material, and tissue retrieval with biopsy tongs. The hollow needle may be replaced by a hollow drill when hard tissue, such as bone, needs to be passed through. The main advantage of the instrument 34 is that the position, orientation and approach trajectory and interaction with the tissue are computer-controlled and navigated with anatomic images of the patient such as MRI 29, CT scan 27 and ultrasound, allowing precise interaction of the instrument with the desired tissue's location shape and volume while avoiding undesired damage to surrounding cells. The Ablation System 3 includes a navigated computer 31-controlled laser 32 configured to be inserted with variable aim aided by exchangeable radiofrequency, ultrasound and irrigation sub systems.

The Ablation System 3 works by destroying undesired material as a target matter 7 of any shape, such as tumors, while preserving surrounding tissue by having the capability of delivering at short range, near/far-field electromagnetic radiation 15 to enhance a desired catalytic or resection effect. In one embodiment, the carrier 32 may also be used to deliver, in situ, by stereotactic manner, drugs such as oncologic medications as well as to take a biopsy by inserting and using a biopsy retriever. A main advantage of the Ablation System 3 relies on its capability to resect with high precision, using a laser 32 beam, a defined tri-dimensional shaped volume 33 within the target matter 7, such as in the case of tumors. When medically indicated, depending on the kind of tumor, to deliver electromagnetic radiation 15 for catalysis at a very short range and also, as previously commented, when needed, for redundant reassurance positioning of a deliverer instrument 34 that carries the subsystems. As shown on FIGS. 1 and 2 the Ablation System 3 may be computer-controlled and may include the MRI 29/CT Scan 27 image fusion, navigation, insertion/torsion robotic control, navigation/insertion merge, and inserted device position subsystems. The subsystems may work together to locate and position accurately the deliverer instrument 34. The navigation of the deliverer 34 instrument may be achieved using anatomic images of the patient obtained with MRI 29 and CT scan 28, obtained while having position marks known as fiducials 35 also aided by anatomic landmarks. The images are then merged using standard DICOM images fusion programs. The position marks 35 are also present and attached to the distal end 36 of the deliverer instrument 34 holder 37 and on the patient. Note that the tip of the deliverer instrument as shown on FIGS. 4 and 5 may be moved by a robotic arm 46 to an anatomic position using the information and programming of a computer that controls the movements of the robotic arm 46. Once in the desired position, the sharp end of the deliverer 40 is withdrawn and the laser 32 is inserted. So, with the laser beam is turned on at previously selected intensities, the laser is aimed by rotation 50 and displacement along its insertion axe 51 in order to produce an ablation volumetric shape accordingly with the volumetric shape and position of the target tissue 7 to be ablated.

Figure 5:
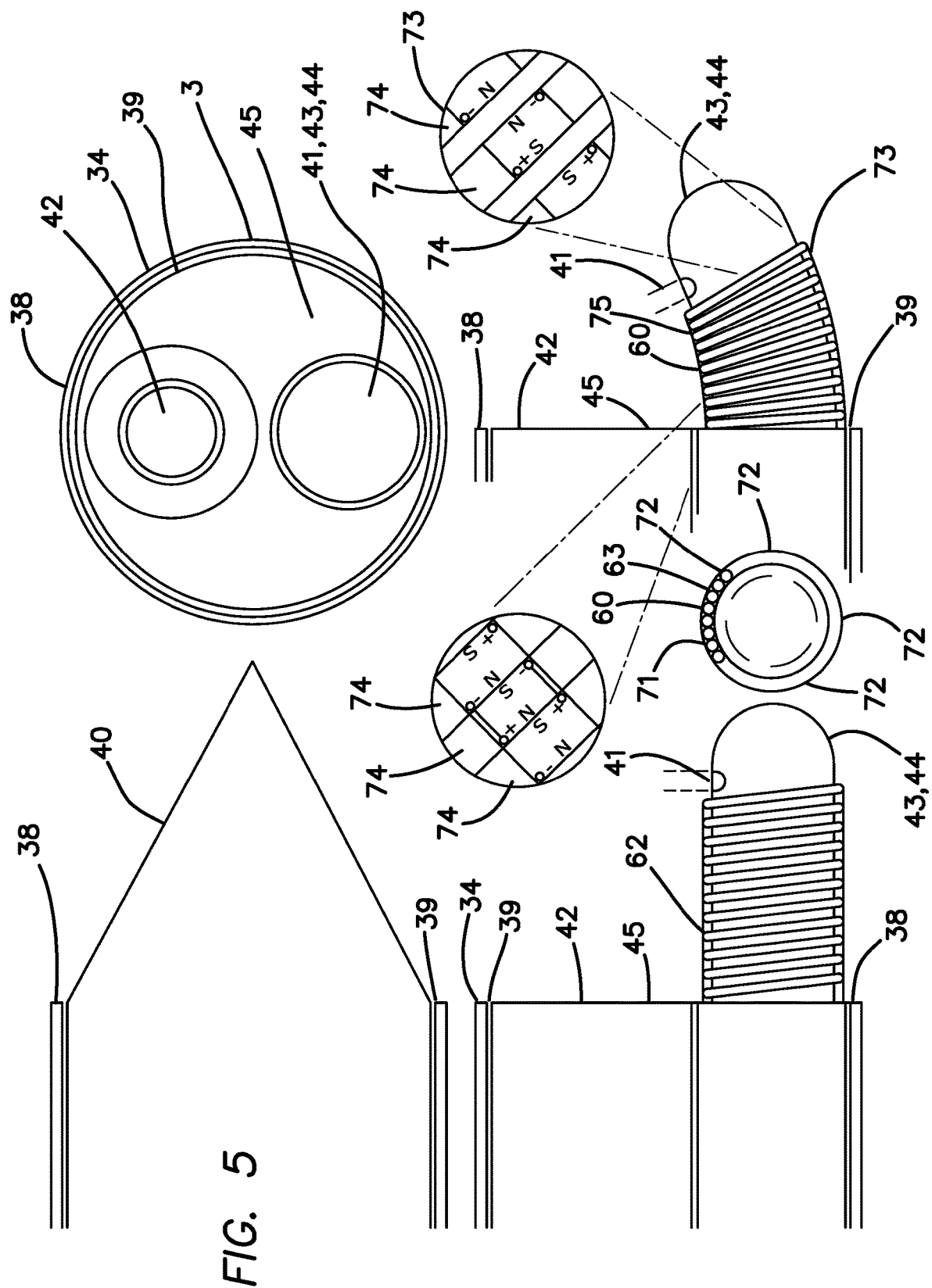
FIG. 5 illustrates a deliverer instrument having a hollow external cylindrical shape with working channels, according to example embodiments.

FIG. 5 shows, as part of the example embodiment, the deliverer 34 that has a hollow external cylindrical shape 38. Inside the external cylindrical shape 38 there is a working channel 39 where different systems may be exchanged. While being inserted, the deliverer instrument 34 may contain on the working channel a cylinder with a pointing edge 40 located on the advancing end, resembling a conic shape. Once in adequate position the internal cylinder acting as a sharp pointing edge 40 is withdrawn. So, inside the working channel 39, the deliverer instrument 34 can be now loaded and able to work with exchangeable subsystems such as a Laser Beam Emission/Aim 41, high resolution camera 42, Emitter/Receiver Radiofrequency 43 and Ultrasound 44. While these exchangeable subsystems may be controlled independently, they serve as a part of the Ablation System 3. Please note that, as an example embodiment, the irrigation (when needed) through the deliverer instrument 34 goes between the subsystems 41, 42, 43, and 44 and the internal cylinder 45, and the drain goes between the internal cylinder 45 and the external cylinder 38. Also note that the working channel 39 may use the laser subsystem 41 and a high resolution camera 42 may be withdrawn in order to use its working channel as a drain. So, once the surgeon decides the best trajectory using computer 31 simulated navigation, the skin is open using a scalpel, then the deliverer instrument 34 equipped with the narrow advancing end 40 is gently advanced by the computer-guided robotic arm 46 and inserted into the patient's body 7 following a planned trajectory 47.

When proper position 48 is reached and reassured using both the position marks/binocular infrared camera 49 and the robotic arm 46 position controls, the occlusive rod 40 is removed from the lumen 39. Then, the deliverer instrument 34 is rotated 50, advanced or retreated 51 with respect to the starting point. Once the systems are ready for proper functioning, the laser beam is turned on and starts the ablation of the planed shaped volume 52. The irrigation/drain system 42 may work simultaneously with the laser beam system 41 in order to cool the area. According to the internal diameter 52 of the deliverer instrument 34 (usually before the laser beam 41 is turned on), a biopsy needle may be used to obtain a tissue sample using the lumen 39 of where the Laser 41, Electromagnetic Radiation 43 and Ultrasound 44 subsystems are loaded and/or exchanged. Withdrawing of the laser system 41 may be necessary to insert into the deliverer 34, the ultrasound system 44 and/or the electromagnetic radiation emitter antenna 43. The ultrasound system 44 may be used for recognition of tumor remnants and as a reassurance of proper position of system 48. The electromagnetic radiation emitter antenna 43 may be used for close range catalysis under the synergy of B0 5. Besides, it may also be employed as an alternative reassurance position 48 finder (see FIG. 4). In other words, the deliverer instrument holder 37 is consequently controlled by the advancing/retreating and rotation of electric motors from the robotic arm 46 (see FIG. 4).

The position of the holder 37 with regard to the patient 55 is monitored and calculated by an infrared binocular computer controlled camera 49 based on the lecture of the position marks 35 of the patient 55 with regard to the position marks 35 of the holder 37 as well as with the movements of the robotic arm 46. So, movement calculations of the computer controlled robotic arm 46 may match the position calculations obtained by the infrared binocular sensor 49 by using the position marks 37 in order to achieve highest reassurance. When properly done, the removal of a tumor by ablation becomes very precise and secure. Please note the advantageous capability to avoid undesired structures, such as important blood vessels, neurologic healthy structures or biologic ducts. As an example embodiment, the laser subsystem provides a double capability to aim the laser beam 41 in multiple angles. The first angle is provided by the robotic arm and the second angle is provided by the bending capability of the laser's tip. A laser mirror may be employed to deflect the laser beam 41. Different laser subsystems with different angles 57 of the mirror may be employed. Note that when the mirror 56 is in a flat position 58, the laser beam 41 goes all the way forward through the main axis 59 of the deliverer device 34. When the mirror 56 is angled, the laser beam 41 is deflected consequently by the mirror 56.

As an example, when the mirror is angled at 45 degrees, the laser beam is deflected 90 degrees from the main axis 59. Having this in mind, the computer 31 programs produce a shooting pattern based on laser beam 41 intensity, duration of every shoot and aiming of every shoot in order to generate a precise and secure resection plan. Another main advantage of the proposed Ablation System 3 is a minimal structural damage the deliverer instrument 34 produces in the surgical approach to the lesion to be removed compared with the one produced with open surgery. Another main advantage of this Ablation System 3 is based on a higher precision of resection based on the mathematical resection planning of the tumors and the capability to obtain MRI 29, CT scan 27 and ultrasound 44 images during the surgical ablation without even moving the patient given that the Ablation System 3, the procedural (operating) room is in the same room as the MRI 29/CT Scan 27. The ultrasound images may be obtained from the ultrasound 44 transducer located on the deliverer instrument 34 as well as from a coupled ultrasound transducer applied by other means. Yet another advantage of the Ablation System 3 with respect to radio-surgery is that tumors 52 that are larger than 3 cm in diameter now can be safely treated without surpassing the ionizing radiation permitted limits of radio-surgery were X-Rays or Gamma radiation are employed.

In one embodiment, the deliverer 34 with the instrument may be computer 31-controlled on its bending by using a computer-controlled array of the novel variable resistance, inductance solenoid VARIS 60 as described herein. Besides, the energy deliverer instrument 34 is able to emit, accordingly to the target material 7 to be catalyzed, a full spectrum of electromagnetic 41, 43/ultrasound 44 energy. The emissions of multiple types may be tuned on harmonic frequencies to produce a synergic effect. Note that the laser 41 may shoot at different angles, because the Ablation System 3 may use manufactured laser cannons shooting at 90, 45 and 0 degrees from the longitudinal axis 59. The laser 41, besides of being used for ablation of tissue to be destroyed, may be also used as any laser for standard interferometer. The deliverer instrument 34 may be connected with optic fiber 61 that transmits the laser beam 41. The deliverer instrument 34 may also include electric cable 62 in order to emit electromagnetic waves from antennas or Ultrasound Transducer Systems 43 and 44. As shown in FIGS. 3 and 4, the deliverer instrument 34 has the capability to interchange subsystems 41, 42, 43, and 44. When needed, given that the strong magnetic field B0 5 and the high frequency electromagnetic radiation B1 15 are already present on catalysis system, magnetic resonance imaging (MRI) 29 may also be integrated on the system 1 in order to retrieve images during catalysis 2 or Ablation 3 procedures. Now with the bending capability of the laser system 41, the beam is able to be emitted at multiple angles and from more positions, added up to the movement of the mirror 56 as well as the displacement and rotation of the instrument 34 along the insertion trajectory 47. In one embodiment, the laser system 41 may work independently from B0 5 and B1 15.

Figure 5A:
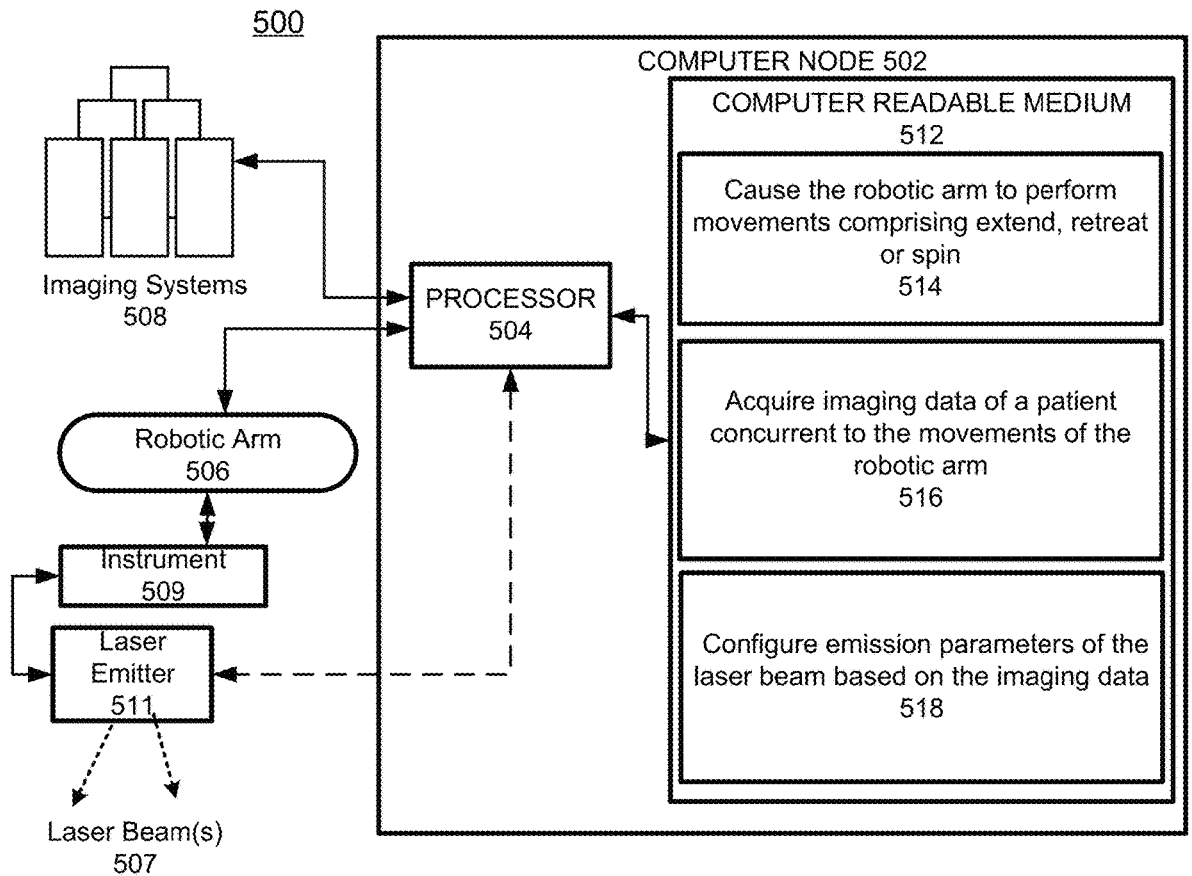
FIG. 5A illustrates a schematic diagram of a system including detailed features of a computer node operatively attached to a robotic arm, according to example embodiments.

FIG. 5A illustrates a schematic diagram of a system including detailed features of a computer node operatively attached to a robotic arm, according to example embodiments.

Referring to FIG. 5A, the example system 500 includes a computer node 502 operatively connected to a robotic arm 506 over a network (wired or wireless). In one embodiment, the computer node 502 may be connected to imaging systems 508 (e.g., MRI, CT scanner, ultrasound device, etc.) over a network to receive imaging data. The computer node 502 may be connected over network to a laser emitter 511 located on (or integrated into) an instrument 509 attached to the robotic arm 506. Multiple other participant nodes or robotic arms may be connected to the computer node 502. While this example describes in detail only one computer node 502, multiple such nodes may be connected to other robotic arms over the network. It should be understood that the computer node 502 may include additional components and that some of the components described herein may be removed and/or modified without departing from a scope of the computer node 502 disclosed herein. The computer node 502 may be a computing device or a server computer, or the like, and may include a processor 504, which may be a semiconductor-based microprocessor, a central processing unit (CPU), an application specific integrated circuit (ASIC), a field-programmable gate array (FPGA), and/or another hardware device. Although a single processor 504 is depicted, it should be understood that the computer node 502 may include multiple processors, multiple cores, or the like, without departing from the scope of the computer node 502 system.

The computer node 502 may also include a non-transitory computer readable medium 512 that may have stored thereon machine-readable instructions executable by the processor 504. Examples of the machine-readable instructions are shown as 514-518 and are further discussed below. Examples of the non-transitory computer readable medium 512 may include an electronic, magnetic, optical, or other physical storage device that contains or stores executable instructions. For example, the non-transitory computer readable medium 512 may be a Random Access memory (RAM), an Electrically Erasable Programmable Read-Only Memory (EEPROM), a hard disk, an optical disc, or other type of storage device.

The processor 504 may fetch, decode, and execute the machine-readable instructions 514 to cause the robotic arm 506 to perform movements comprising extend, retreat or spin. The processor 504 may fetch, decode, and execute the machine-readable instructions 516 to acquire imaging data of a patient concurrent to the movements of the robotic arm 506. The processor 504 may fetch, decode, and execute the machine-readable instructions 518 to configure emission parameters of a laser beam 507 based on the imaging data.

Figure 5B:
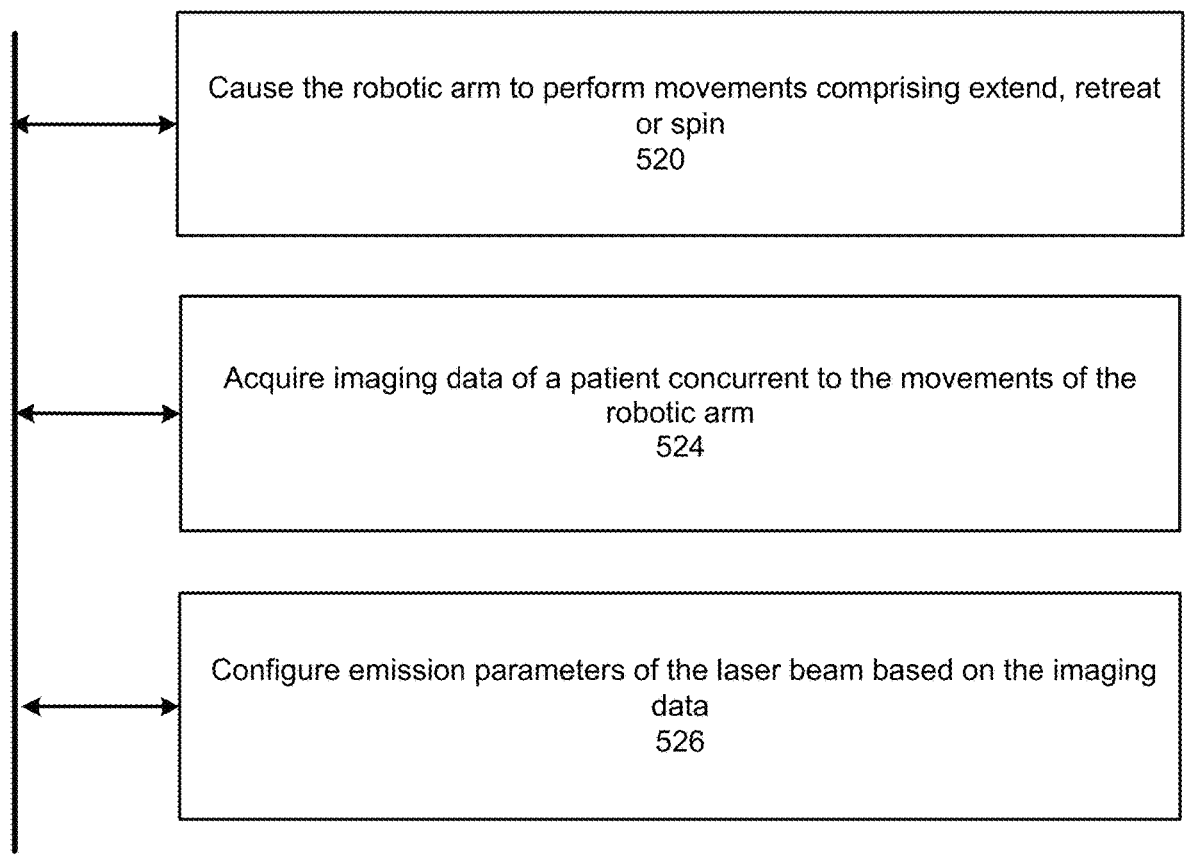
FIG. 5B illustrates a flow diagram of a method for computer-assisted robotic ablation.

FIG. 5B illustrates a flow diagram of a method for computer-assisted robotic ablation. Referring to FIG. 5B, the method 510 may include one or more of the steps described below.

FIG. 5B illustrates a flow chart of an example method executed by the computer node 520 (see FIG. 5A). It should be understood that method 510 depicted in FIG. 5B may include additional operations and that some of the operations described therein may be removed and/or modified without departing from the scope of the method 510. The description of the method 510 is also made with reference to the features depicted in FIG. 5A for purposes of illustration. Particularly, the processor 504 of the computer node 520 may execute some or all of the operations included in the method 510.

With reference to FIG. 5B, at block 520, the processor 504 may cause the robotic arm to perform movements comprising extend, retreat or spin. At block 524, the processor 104 may acquire imaging data of a patient concurrent to the movements of the robotic arm. At block 526, the processor 104 may configure emission parameters of the laser beam based on the imaging data.

Figure 5C:
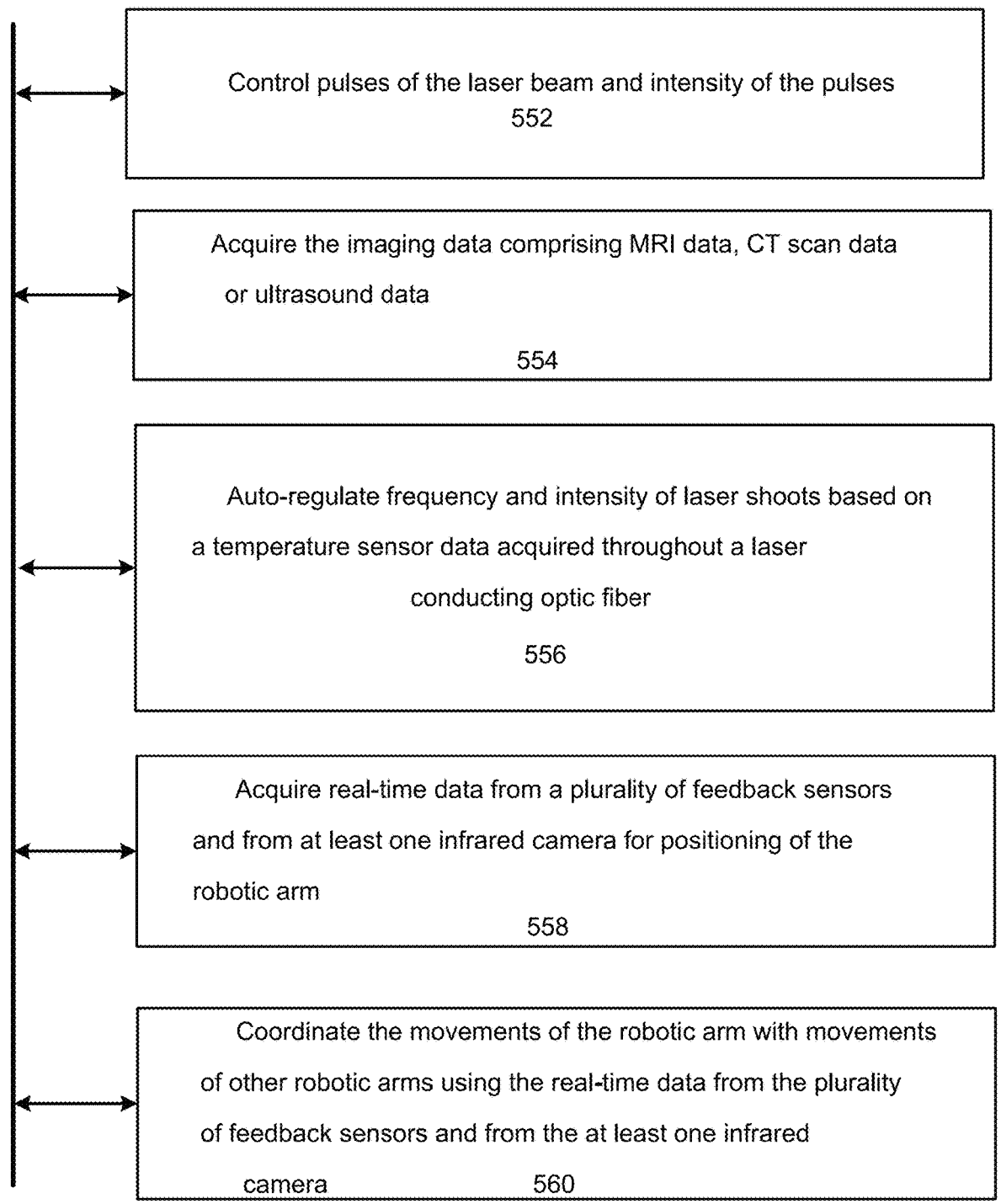
FIG. 5C illustrates a further flow diagram of a method, according to example embodiments.

FIG. 5C illustrates a further flow diagram 550 of an example method, according to example embodiments. Referring to FIG. 5C, the method 550 may also include one or more of the following steps. At block 552, the processor 504 may control pulses of the laser beam and intensity of the pulses. At block 554, the processor 504 may acquire the imaging data comprising MRI data, CT scan data or ultrasound data. At block 556, the processor 504 may auto-regulate frequency and intensity of laser shoots based on a temperature sensor data acquired throughout a laser conducting optic fiber. At block 558, the processor 504 may acquire real-time data from a plurality of feedback sensors and from at least one infrared camera for positioning of the robotic arm. At block 560, the processor 504 may coordinate the movements of the robotic arm with movements of other robotic arms using the real-time data from the plurality of feedback sensors and from the at least one infrared camera. Note that the emission parameters of the laser beam may include direction, intensity and duration of the emission of the laser beam configured to destroy pre-defined shape and volume of cellular tissue of a body of a patient.

In one embodiment, a novel Electromagnetic Motor System is provided. The Electromagnetic Motor System may include at least two permanent or electrically induced magnets connected to electric circuits. The multiple magnets are arranged on elastic substrates in order to produce movements of attraction and repulsion amongst each other using the magnetic field force. Accordingly, with the intensity and direction of the magnetic field exerted on every magnet, each magnet is therefore, forced to move on complex trajectories. Given that multiple magnets interact with each other, complex movements of the substrates are enabled according to the relative position of each magnet and the shape and frequency of the intensity of current delivered through each coil. Thus, enabling the substrate to become a material that may behave as a multi-directional, multi-shape, multi-frequency movement emitter (multi-directional motor/muscle or advanced fabric that vibrates according to desired shapes or frequencies—e.g., on epithelial/mucosal surfaces or as an advanced sound emitter). The substrate may also produce electric current when the magnets are moved relative to each other. Detection/Programming of/for solenoid movement may also be achieved by monitoring/controlling the electric intensity on coils for producing/reproducing/transmitting the movements of the substrate into another substrate.

According to the exemplary embodiment, the novel concept presented herein relies on multi-pivoting motor/generator based on electromagnetic repulsion/attraction forces amongst magnets. The example embodiment works by deploying multiple magnets that interact with each other's magnetic neighboring fields, employing attraction and repulsion forces and, therefore, generating movement from electricity by creating interacting magnetic fields or generating electricity from movement of the magnets from original relative position to a new relative position. This may generate a wide range of simple to complex, uni-directional to multi-directional movements obtained from the electric energy. So, as discussed above, the novel multi-pivot device may also transform kinetic energy into electricity and may act as an advanced kinetic energy vector field sensor/recorder/reproducer given that every electric signal may correspond to each different electromagnet uniquely deployed at known spatial relative positions within the elastic frame.

Figure 6:
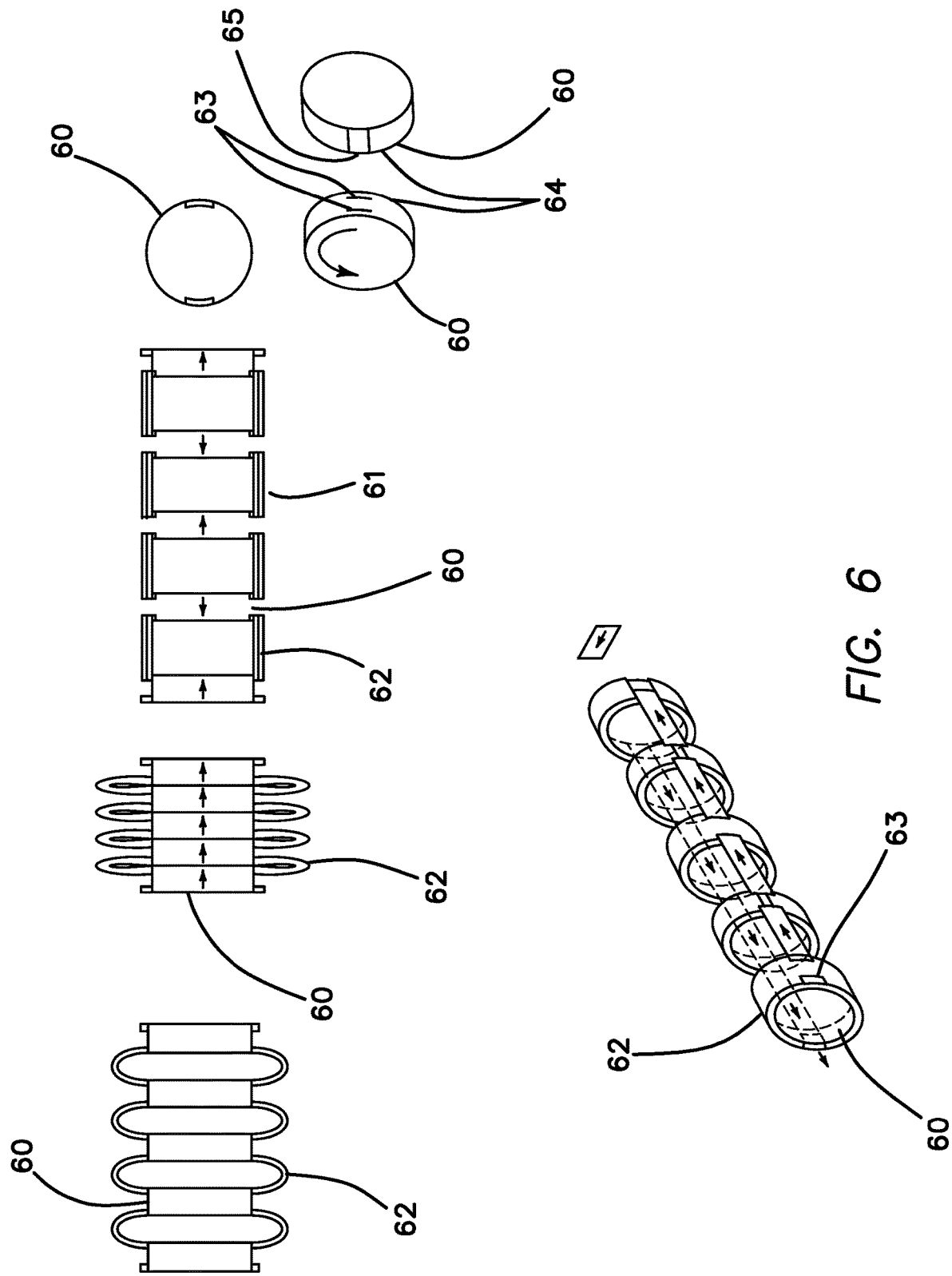
FIG. 6 illustrates an example engine/generator with multiple degrees of freedom that produces kinetic force from electromagnetic force and vice verse while using a multi pivot elastic substrate, according to example embodiments.

FIG. 6 illustrates an example engine/generator with multiple degrees of freedom that produces kinetic force from electromagnetic force and vice verse while using a multi pivot elastic substrate, according to example embodiments.

FIG. 6 shows a novel engine/generator with multiple degrees of freedom that produces a kinetic force from an electromagnetic force and vice verse while using a multi-pivot elastic substrate 62. The engine includes interacting magnets 60 on an elastic substrate 62. Given that each electromagnet 60 is able to produce a magnetic repulsion/attraction force over neighbor electromagnets 60 and given that each of the electromagnet/permanent magnets interact with each other according to the direction and intensity of the electric current, the result is a substrate 62 that produces electromagnetic powered mechanical movement in multiple patterns depending on type of the elastic substrate 62 and the sequence of electric current through the electromagnets 60.

Note that such elastic substrate 62 is capable to also produce mechanical vibration in order to generate tactile sensations when applied on epithelial or mucosal surfaces. The magnets 60 are capable to produce electric currents when their magnetic fields interact with each other because of magnets' movement. FIG. 6 shows the elastic substrate 62 that contains multiple solenoids 60 that are advanced solenoids (known as VARIS) arranged on strips of elastic substrate 62, where the solenoids are attached to each other by the elastic and electrically conductive substrate 62 in two-sided attaching and electrically conductive bands 62 in order to produce a linear expansion/contraction of the strip of the elastic substrate.

Note that the feeding electrodes 63 of the solenoid 60 are located on the circular wall 64. An electrically conductive plaque 65 may be located on the opposite side of the circular wall. Given that the elastic substrate 62 includes one electro-conductive band 62 at each side, and the solenoids 60 are dish shaped, when coincident, the electric current goes as small arrows point through the closest electrode 63, runs through the solenoid 60, exits through the far electrode of the same solenoid 60 and continues through the elastic band 66 to the next solenoid and so on. If the solenoid is rotated 180 degrees, the electro-conductive plaque 65 simply passes the electric current to the next solenoid 60, but therefore the rotated electrodes 63 feed the solenoid 60 in an inverse direction, reversing also the direction of the magnetic field created by the solenoid 60. The electro-conductive plaque 65, located on the opposite side of the solenoid's electrodes 63 connects to the following electro-conductive band and so on. Note that in order to produce a change in the direction of the magnetic force of each solenoid 60, each solenoid may simply be rotated 180 degrees. So the example embodiment allows each strip to produce expansion as well as contraction depending on the rotational position of the dish shaped solenoids 60 as shown on FIG. 6. In order to produce an attraction effect, the current direction of the magnetic field must be the same between each next solenoid 60 and the direction of the electric current therefore must be the same between each solenoid and the next. Consequently, in order to produce an expansion effect, alternated solenoids 60 may be rotated 180 degrees, so that the current direction and the magnetic force are alternated on the solenoids 60 of the strip as shown on the expanded strip case shown in FIG. 6.

Besides, not that if the current is applied at variant frequencies, the solenoids will vibrate at such frequencies. If the solenoids, while fed with electric current are moved, an additional electric signal is produced and may be detected in order to sense kinetic movement, depending on the magnetic interaction between solenoids and the circuit connections. Obviously, in order to close the circuit, an electro-conductive band may also close the electric gap between the electric plaque 65 and one of the electrodes 63 of the same solenoid 60 as shown in FIG. 6.

Figure 7:
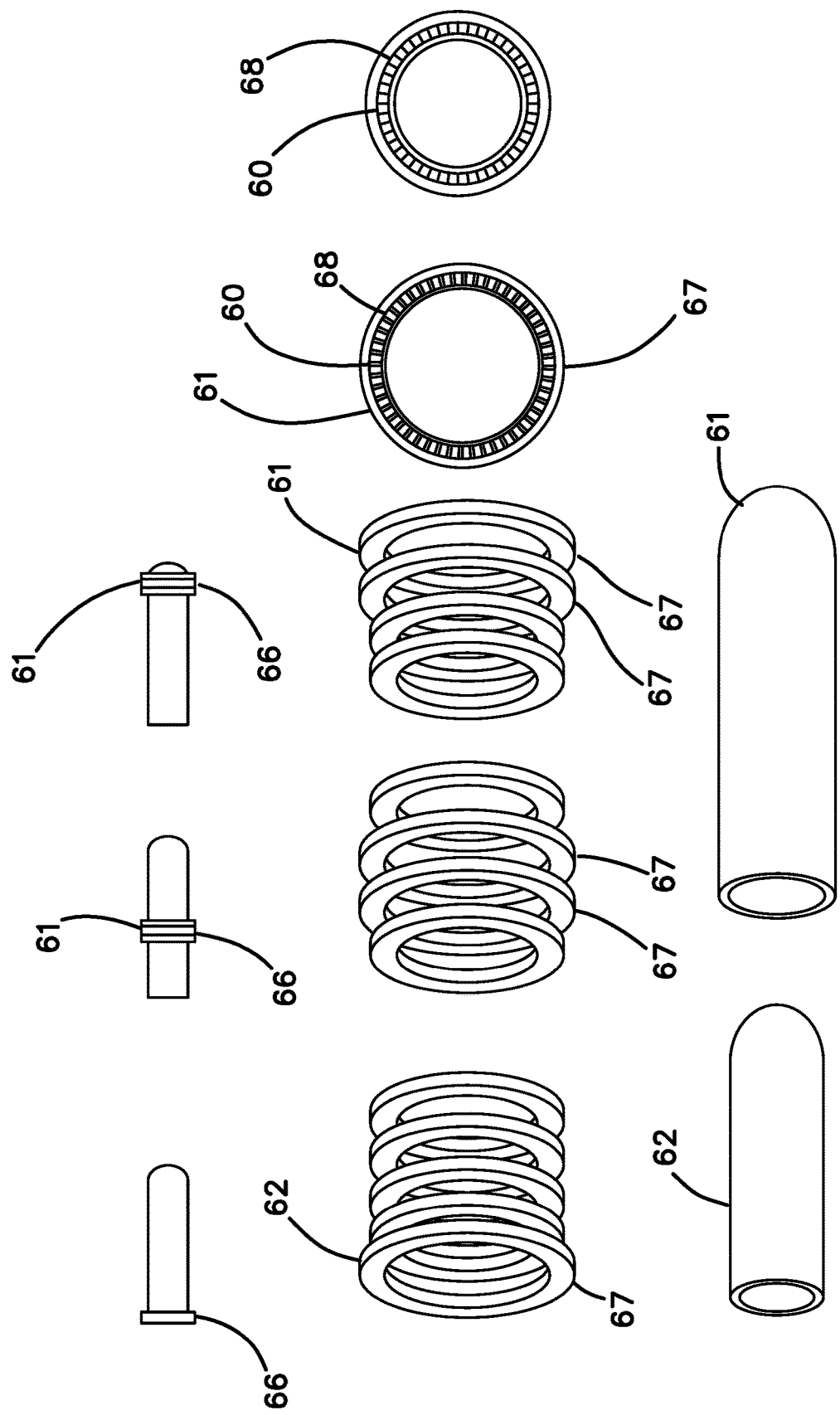
FIG. 7 illustrates a mechanism of bending and expansion of a deliverer instrument where VARIS electromagnets are deployed on an elastic substrate, according to example embodiments.

FIG. 7 illustrates a mechanism of bending and expansion of a deliverer instrument where VARIS electromagnets are deployed on an elastic substrate, according to example embodiments.

FIG. 7 further illustrates engine/generator with multiple degrees of freedom for deliverer instrument 34 where electromagnets VARIS 60 and an elastic wall 62 of the deliverer instrument 34 that provides for bending and expansion like movements. How the bending is possible relies in the electromagnet array of a number (four, for instance) of circuits that loops around the laser system 41. Note that every of the four circuits are made of a succession of solenoids 60 separated by lengths of a coil. Together these loop around the elastic walls of the laser 41/Electromagnetic Antenna 4/Ultrasound 44, coinciding the solenoids 60 of the same circuit on the same side of the walls as shown in the FIG. 4. So, an embodiment of subsystems 41, 43, and 44 includes walls with arrays of high inductance mini solenoids 60 as shown on FIG. 7. The high inductance solenoids 60 may be used as possible components in most of the preferred embodiments of the Catalysis System 2, where because of the upgraded antennas 13 they may provide for the TAM 16 like antennas.

With regard to the Ablation System 3, the bending capability provided by the array of the high inductance solenoids 60 makes this variable resistance inductance solenoids VARIS 60 to be indispensable components for the novel technologies used by the Ablation System 3. Note that for expansion purposes, the direction of the magnetic force of each solenoid 60 may be repelled by equal polarity of the adjacent solenoid 60 producing an increment in the distance among each solenoid 60 deployed as a ring like 68 array on the elastic wall 62 depicted in FIG. 7. The high inductance solenoids 60 are very useful because of their capability to produce important attraction/repulsion magnetic force through the elastic substrate 62 they are integrated into. The array 63 of solenoids 60, accordingly to a computer programmed sequence, may receive electric current to orderly produce sequential magnetic fields that interact with multiple other solenoids 60 (according to when and which circuit gets electric current passing through it).

As explained above, for contraction, the odd solenoids 60 receive electric current in a contrary direction than the even solenoids 60 within the ring-shaped 68 array deployed as two serial circuits (not in parallel, given that that reduces total inductance) on each ring. As shown on FIG. 7, a sequence 66 of expanded rings 68 is synchronized to run along or even expand all of the elastic wall 62 which may be very important for separation (dissection) of very delicate tissue (like brain parenchyma) during a procedure. As discussed above, given the direction of the current, the north of each magnetic field tries to get away from any other north pole next to it and so on. The same thing happens with the south pole of each of the solenoids 60 next to them producing the bending of the deliverer instrument 34 as shown on FIG. 5. So, if the repulsion occurs along the wall of the elastic substrate 62, an elongation on the longitudinal axis of the cylindrical elastic surface 62 is produced. In other words, there are multiple (e.g., four) independently controlled circuits 67 of a simple coated wire used in solenoids 60 at preset distances from each other.

The preset distances allow the array of solenoids 60 of each circuit to be rolled into the elastic wall 62 that covers the subsystems 41, 43, 44 bending it. Thus, such looping may form a pile 71 of the solenoids 60 that belong to the same circuit at each of the four sides 72 of the electromagnetic elastic wall 62 of the deliverer instrument 34 where electromagnets VARIS 60 are deployed on the elastic wall 62 of the deliverer instrument 34 that provides bending and expansion like movement.

Note that mechanical energy may also be transformed into electromagnetic energy by using the VARIS 60 on array 63 when the magnetic fields 76 of the VARIS 60 are moving with respect to each other's magnetic fields 76. By making this array 38 of the solenoids 60 to work like a movement/vibration sensor, this feature becomes important when the elastic wall 62 approaches every time closer to an artery. The pulsation of the vessel may then be detected by the computer before catastrophic bleeding occurs. The array of the solenoids 60 according to the frequency and intensity of electric current may also be used to make the array 38 located on the elastic wall 62 to vibrate. Such vibration may then be used to transform the array 38 and the elastic wall 63 hosting it into a sonic/ultrasonic scalpel if the tissue needs to be cut, heated or simply gently removed by vibration as in the case of calcium removal when inside the lumen of an artery or prostatic tissue when inside the urethra. It is important to mention that a controlled bending capability is mostly needed on many medical specialties.

In order to avoid electromagnetic energy from outer sources affecting the performance of this mini bending engine, an electrostatic cover is provided to the array 38 of solenoids 39. Note that any of the subsystems can be included within the elastic walls that contain the arrays 38 of the solenoids 60 within elastic walls 62. The walls 62, according to the internal connections of the solenoids 60, may produce mechanical work from electromagnetic energy. As shown in FIGS. 4, 5 and 6, a tubular wall 62 with the capability of bending and expanding is provided. The expansion occurs when the designated circuits that produce a repulsion force 64 between each solenoid may be changed according to different needs and shapes without departing of the spirit of the instant disclosure. For instance, the elastic wall 62 may be also used as the tip of a catheter or endoscope, disembodied from the deliverer instrument 34. Independent strips may be located, attached and combined is a custom manner to mobilize articulations as electromagnetic muscular fibers in order to upgrade robotic science.

FIG. 7 also depicts the internal architecture of the advanced solenoids 60 where configuration includes looped sheets 69 where every sheet includes multiple intersecting tracts 97 of electric conductive material 98 that allow electrons while running on curvilinear paths, to add up electromagnetic energy. The standard VARIS 60 has a distinctive feature and novelty over standard solenoids that the width 103 of the electro conductive material 102. The plane 103 that encases the turn 104 of the material 102 is bigger than in other planes. So, the electro-conductive material 102 provides multiple paths 96 for the electrons. This design increases resistance and inductance. When necessary, in order to provide this novel electronic component 60 with a safe guard mechanism, a semi conductive electrical material 104 may be placed separating a second adjacent rolled along VARIS 39. So, the combination of both adjacent couple of VARIS 60 separated by the electric semi-conductive material 104 produces a capacitor effect that enables electricity to jump to the second VARIS 60 if the capacitance is surpassed, avoiding excessive heat. The example combination produces an Inductance Capacitance Resistance resonant microcircuit 106, providing important technical advantages. This novel configuration is called VARIS-C 91 capacitor 107.

One of the technical advantages is in the capability of providing the Ablation System 3 with a micro-circuit antenna that fits in the deliverer instrument 33 and may emit on different frequencies of far-field electromagnetic radiation 15. The tridimensional feature of the VARIS 39 and VARIS-C 107 may include multiple loops 108 of coated wire 109 that first covers all the width 110 of the first layer or roll 111 before going to the next layer 112 and so on. The coated wire 109 presents fluctuations on the no-conductive capability of the coating in order to provide multiple paths 97 for the electrons to travel each loop 108 once a certain voltage level is achieved.

In yet another example embodiment, a super capacitor improved magnetic charging system is provided.

Figure 8:
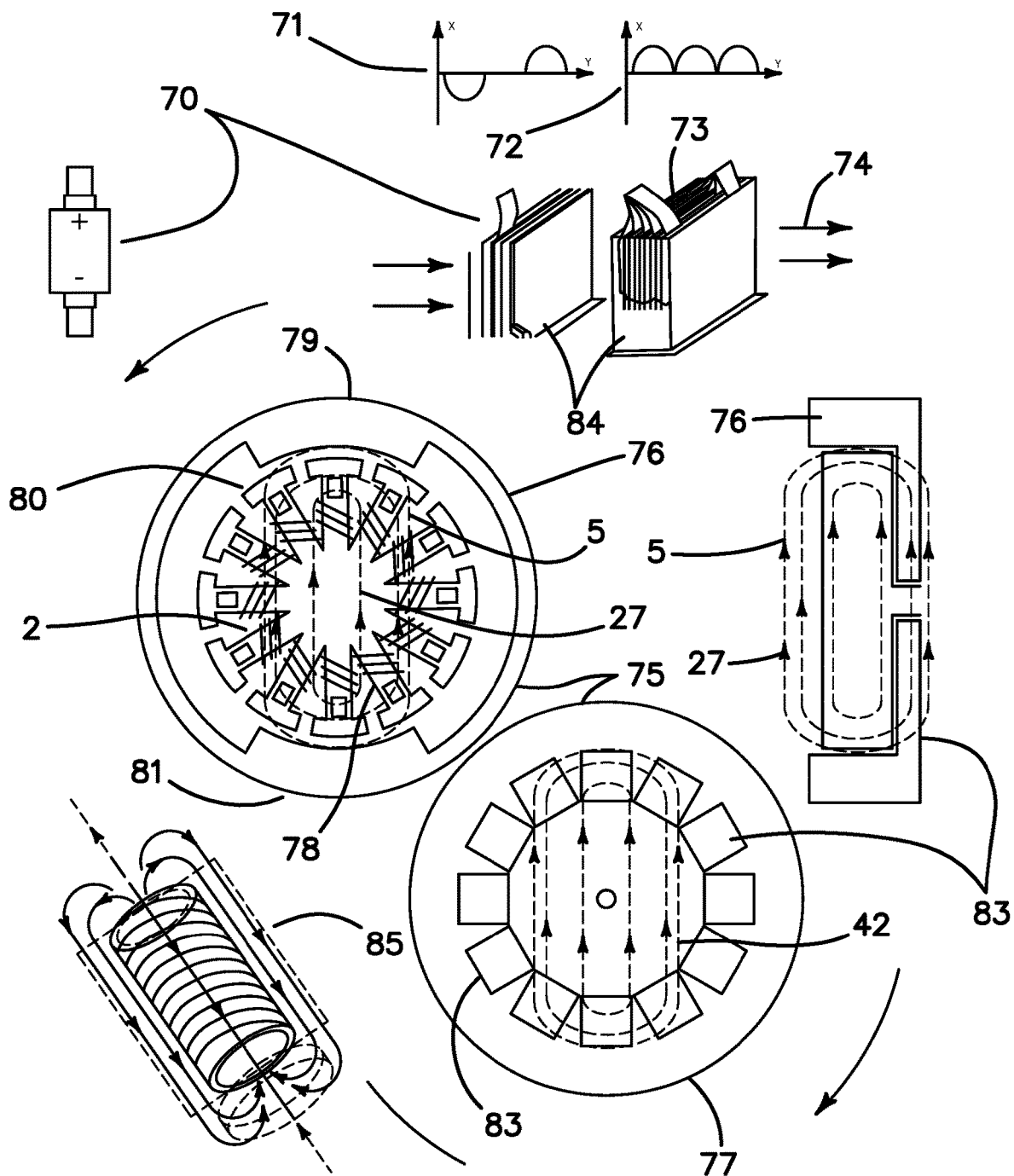
FIG. 8 illustrates electromagnetic resonance Catalysis System for improved recharging of ultra capacitors, according to example embodiments.

FIG. 8 illustrates electromagnetic resonance Catalysis System for improved recharging of ultra capacitors, according to example embodiments.

FIG. 8 shows an example embodiment of the electromagnetic resonance Catalysis System 2 used on preferred mater 7 that mostly contains ions. In case of ions, it is not necessary to employ an emitter antenna to affect molecules. So in the case of ionic electricity storage devices 70, the resonant Catalysis System 2 provides a novel way to improve the recharging of super capacitors 70. Thus, using the magnetic field B0 5 now may also be alternate 71 as long as it remains unidirectional 72. Given that Super Capacitors 70 usually store energy by simply grouping separately negative and positive charged ions, and all ions are affected by a magnetic field, the Catalysis System 2 enhances the charging by simply placing the ions of Super Capacitors 70 under the influence of the unidirectional 72 magnetic field B0 5, variable or not, with the micro membranes 73 of the Super Capacitors 70 placed in perpendicular position with regard to the magnetic force lines 74 as shown in FIG. 8.

The novel Catalysis System 2 may be deployed on a brushless DC electric motor 75 with the rotor 76 including a permanent magnet 77. For example, the brushless DC electric motor of the robotic arm 46 or even the one used in an electric car may be used. The stator 78 includes multiple electromagnetic coils 79 that produce rotation of the rotor 76 by presenting a magnetic force 77 of attraction 78 to the poles of the permanent magnet 77. So the North Polarity 79 of the permanent magnet 77 is constantly attracted by a rotating South Polarity 80 on the electromagnetic coils 60 as well as the South Polarity 81 present on the permanent magnet 77 is constantly attracted by the rotating North Polarity 82 produced by the electromagnetic coils 60. Note that although the polarity of the magnetic fields changes on the stator 78 coils, the poles of the permanent magnet 77 are always attracted by the opposite polarity 80, 82. Such unidirectional 72 variable magnetic field allows for placement of a number of super capacitors 70 attached to the permanent rotating magnet 77 in order to better charge and store energy by using the energy from the unidirectional magnetic variant magnetic field 72. FIG. 8 shows the preferred places for attachment 83. So the condition discussed above with regard to exposing the membranes 73 of the super capacitors 70 to a perpendicular unidirectional 74 variable magnetic force lines is achieved. The frequency of variation of the magnetic force 74 is in this case related to the angular speed of rotation of the electric motor 75. Please notice that square-shaped 84 super capacitors 70 are better charged by being exposed perpendicularly to the magnetic force lines in the core of the solenoid or on the external loops of the magnetic lines of force. The rolled-shaped ultra capacitors are better charged while being exposed where the magnetic lines of force are concentric as well as eccentric as shown in FIG. 8 at both ends of a tubular solenoid 85.

Figure 9:
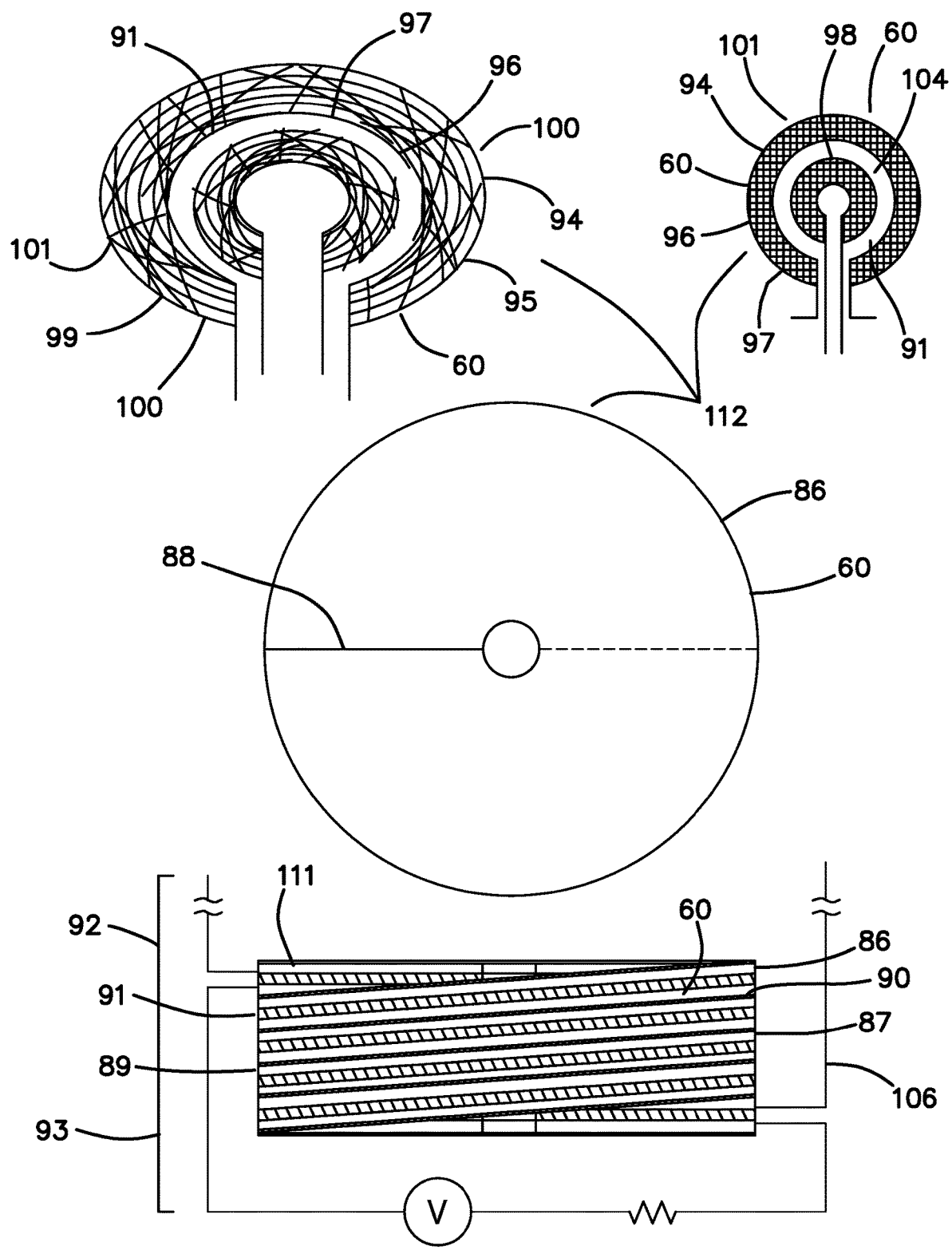
FIG. 9 illustrates examples of VARIS and VARIS-C including looped sheets with intersecting tracts of electric conductive material, according to example embodiments.

In one embodiment, a novel solenoid/capacitor technology is provided. FIG. 9 illustrates examples of VARIS and VARIS-C including looped sheets with intersecting tracts of electric conductive material. The novel Solenoid/Capacitor technology provides higher magnetic field intensity by serial connected rolls of looped wire 96, being every roll with multiple intersecting tracts 97 of electric conductive material 98 that allow electrons, while running on curvilinear paths, to add up electromagnetic energy. Applications of this technology are the Variable Resistance and Inductance Solenoid (VARIS) and Variable Resistance and Inductance Solenoid/Capacitor (VARIS-C) as well as the upgrading of the winding of any electric motor. The VARIS-C behaves as a resonant microcircuit, providing important technical advantages such as variable frequencies as in micro-strip antennas and higher performance novel multi pivoted electric motors/generators.

Given that the micro-strip emitter antennas are limited to preset frequencies of the printed circuit that are present on the TAM antennas, it was necessary to design printed circuit variable frequency emitter antennas using novel solenoid/capacitor technology to adjust to the Larmor frequency of the target matter to be catalyzed. The novel technology is also designed to enhance the performance of the novel Electromagnetic Multi Pivot Motor System and Method given the higher inductance provided compared with other magnets. This novel technology applied on the winding of electric motors/generators provides higher inductance, enabling improved performance.

FIG. 9 shows the example embodiments of the VARIS 60. This implementation becomes necessary for the best performance of both, the Resonant Catalysis System 2 and the Ablation System 3. Thus, FIG. 9 includes the internal architecture of the advanced solenoids 60 configured with looped sheets or plaques 86 where every sheet includes multiple intersecting tracts of electric conductive material 87 that allow electrons while running on curvilinear paths, to add up electromagnetic energy. The standard VARIS 60 has as distinctive feature and novelty over standard solenoids that the width 88 of the electro-conductive material 87, on the plane 89 that encases a loop 90 of the material 87, is bigger than in other planes. So the electro-conductive material 87 provides multiple paths 86 for the electrons. This design increases resistance and inductance. When necessary, in order to provide this novel electronic component 60 with a safe guard mechanism, a semi-conductive electrical material 91 is placed separating a second adjacent rolled along VARIS 60. So, the combination of both adjacent couple of VARIS 60 separated by the electric semi-conductive material 91 produces a capacitor effect that enables electricity to jump to the second VARIS 60 if the capacitance is surpassed, thereby avoiding excessive heat.

The combination produces an ICR (Inductance, Capacitance, Resistance) resonant micro-circuit 92 providing important technical advantages. This novel configuration is called VARIS-C 93 (Capacitor). One of the technical advantages relies in the capability of providing the Ablation System 3 with a micro-circuit antenna that fits in the deliverer 34 instrument and may emit on different frequencies of far-field electro-magnetic radiation 15. So, with regard to the Catalysis System 2, the micro-strip emitter antennas 16 are limited to preset frequencies of the printed circuit that are present on the TAM 16 antennas. Note that the configuration of the VARIS 60 for micro-integrated printed circuits 94 in FIG. 9 includes ellipsoid 95 as well as circular 96 areas (sheets) that contain multiple intersecting electrically-conductive lines 97 in order to increase resistance and inductance as a function of intensity and frequency. The standard solenoids 60, when printed as micro-integrated circuits 94, are simply semi parallel or parallel circular narrow separated lines. As mentioned above, the frequency of emission of electromagnetic radiation B1 15 must be tuned in order to match the Larmor frequency (also referred to as precession frequency of protons) of selected chemical elements. In other words, when the VARIS 60 is designed and shaped as a micro-printable circuit 94 emitter/receiver antenna and or solenoid as shown in FIG. 9, given that printing is performed in two dimensions, the micro VARIS 60 is shaped as a number of semicircular 98 or semi ellipsoidal 99 wide cumulus 100 of electro-conductive material 97 that presents multiple intermingled paths 101 for the electrons to travel.

As mentioned above, the standard VARIS 60 has a distinctive feature over standard solenoids that the width 102 of the electro-conductive material 91, located on the plane 89 that encases the loop 90 of the material 97, is bigger than in other planes. Thus, the electro-conductive material 97 provides multiple paths 101 for the electrons. This design increases resistance and inductance. The anticipated problem when using the VARIS 60 configuration is that multiple paths 101 provide more resistance and inductance, but may also generate more heat.

When necessary, in order to provide this novel electronic component 60 with a safe guard mechanism, a semi conductive electrical material 91 is placed separating the second coupled 111 adjacent spiral loop or plaque 90 positioned along of an intermingled second VARIS 60. So the combination of the adjacent couple of VARIS 60 separated by the electric semi-conductive material 91 produces a capacitor effect that enables electricity to jump to the second VARIS 60 if the capacitance is surpassed, avoiding excessive heat. The combination produces an ICR (Inductance, Capacitance, Resistance) resonant micro-circuit 112 providing important technical advantages. This novel configuration is called VARIS-C 112 (Capacitor). One of the technical advantages lies in the capability of providing the Ablation System 3 with a micro-circuit antenna that fits in the deliverer 32 instrument and may emit at different frequencies of far-field electro-magnetic radiation 15.

Figure 10:
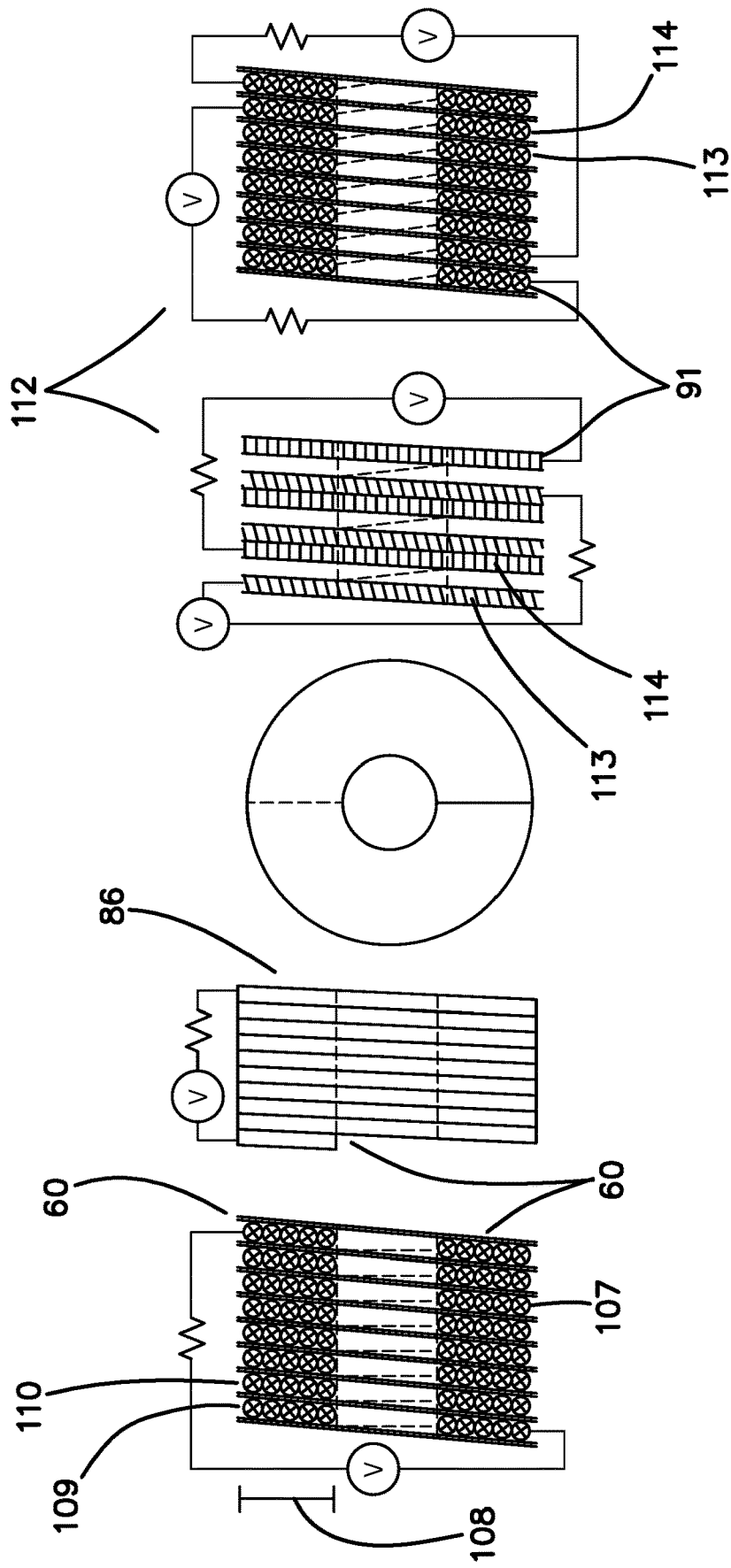
FIG. 10 illustrates the exemplary embodiment of the VARIS and VARIS-C with looped coil spiraled on sub sequential planes where every sheet includes coated wire intersecting tracts of electric conductive material, according to example embodiments.

FIG. 10 illustrates the exemplary embodiment of the VARIS and VARIS-C with looped coil spiraled on sub sequential planes where every sheet includes coated wire intersecting tracts of electric conductive material.

FIG. 10 shows how the winding of the coils of an electric motor is implemented with a number of serial connected rolls of coated wire each contained on consecutive planes encasing the looping to the axe, in order to form sheets 96. The wire may have multiple breaches on the coating enabling multiple intersecting tracts 97 of electric conductive material 98 that allow electrons, while running on curvilinear paths, to add up electromagnetic energy more efficiently. As discussed above, this novel architecture of winding has a distinctive feature and novelty over standard coils given that the width 103 of the electro-conductive material 102 located on the plane 103 that encases the turn 104 of the material 102 is bigger than in other planes. Thus, the electro-conductive material 102 provides multiple paths 96 for the electrons. This design, advantageously, increases resistance and inductance.

Note that VARIS 60 as well as the VARIS-C 112 may be air-cored or iron/ferrite-cored (also be looped around ferromagnetic material such as mini-iron cable, allowing the magnetic field to increase in intensity tens to hundreds fold). Given its higher inductance, the Q factor is bigger. A Bitter type electromagnet may have a resemblance with this highly efficient solenoid 60 with the difference that the Bitter type, instead of looped wire or a thin layer (or printed on a micro circuit), may use big parallel or helicoidally shaped plaques, and may be used for ultra-high inductance (0.5 to 34 Tesla).

It may be cooled with fluids (ions free water) that run along the plaques and the Bitter type solenoid usually works at sub-zero temperatures. The Bitter electromagnet is not used as antenna and does not have the solenoid-capacitor configuration. The Bitter electromagnet cannot be printed and does not contain multiple loops of wire forming a sheet. Besides, standard coil winding with multiple loops of wire encased on a helicoidally shaped plane are not designed with variable coating interruptions along their path. High frequency receiving/emitting antennas (air-core) or low frequency receiving/emitting antennas (ferrite/iron core) are improved by this example embodiment. As mentioned above, the layers 96 may be parabolic-shaped in order to combine a high number of wire loops 108 and multiple focusing mini-parabolic discs. Also, mentioned before as part of the VARIS 60 technology, the solenoid-capacitor configuration is comprised on tridimensional embodiments and given that the VARIS 60 comprises multiple loops 101 on a thin layer 113, it is now possible to intermingle a second 114 thin layer as shown on FIG. 10 where electric semi-conductive material 91 is placed between these two thin layers 113 and 114 that belong to two different solenoids, creating a couple of intermingled solenoids that also behave as a capacitor 112. Therefore, resonance occurs, as in this case, in a series circuit when the supply frequency causes the voltages across L and C to be equal and opposite in phase. The resonant circuits can be also used in various forms such as in AC mains filters, noise filters and also in radio and television tuning circuits producing a very selective tuning circuit for the receiving of the different frequency channels. Note that this novel electronic component may also have valuable applications other than upgrading the Catalysis and Ablation Systems 2, 3, such as to benefit induction welding/melting, advance of electromagnetic fulguration/coagulation technologies on surgery, etc. This VARIS/VARIS-C (60,112) arrays may also be employed to better receive the energy of far-field (waves) or even near-field electromagnetic radiation and transform it into electric signals or energy. Please note that FIG. 10 shows another embodiment of the advanced internal architecture of the VARIS 60 and VARIS-C 112 where the winding of the wire 107 is implemented as a number of serial connected spiral-shaped rolls 109 of coated wire 107, each contained on consecutive planes. Note that, in the FIG. 10, for explanatory purposes, inside of each wire 107, the direction of the electric current is indicated by the symbols "x" and ".." So, the "x" (as the tail of an arrow) represents the electricity traveling in a perpendicular and dis-approaching fashion (for the reader) of the piece of paper where the wire is printed. The dot "." is printed within the figure that represents the wire, an approaching direction (for the reader) is represented. Same symbols may be applied for the wire having multiple breaches on the insulation of the wire coating to enable multiple intersecting tracts 97 of electric-conductive material 98 that may allow electrons, while running on curvilinear paths, to add up electromagnetic energy more efficiently. So, as explained above, this novel architecture on winding comprises a distinctive feature and novelty over standard coils given that the width 108 of the electro-conductive material 101 located on the plane or roll that encases the loops of the material 101 is bigger than in other planes. Thus, the electro-conductive material 101 provides multiple paths for the electrons. This design increases resistance and inductance.

Figure 11:
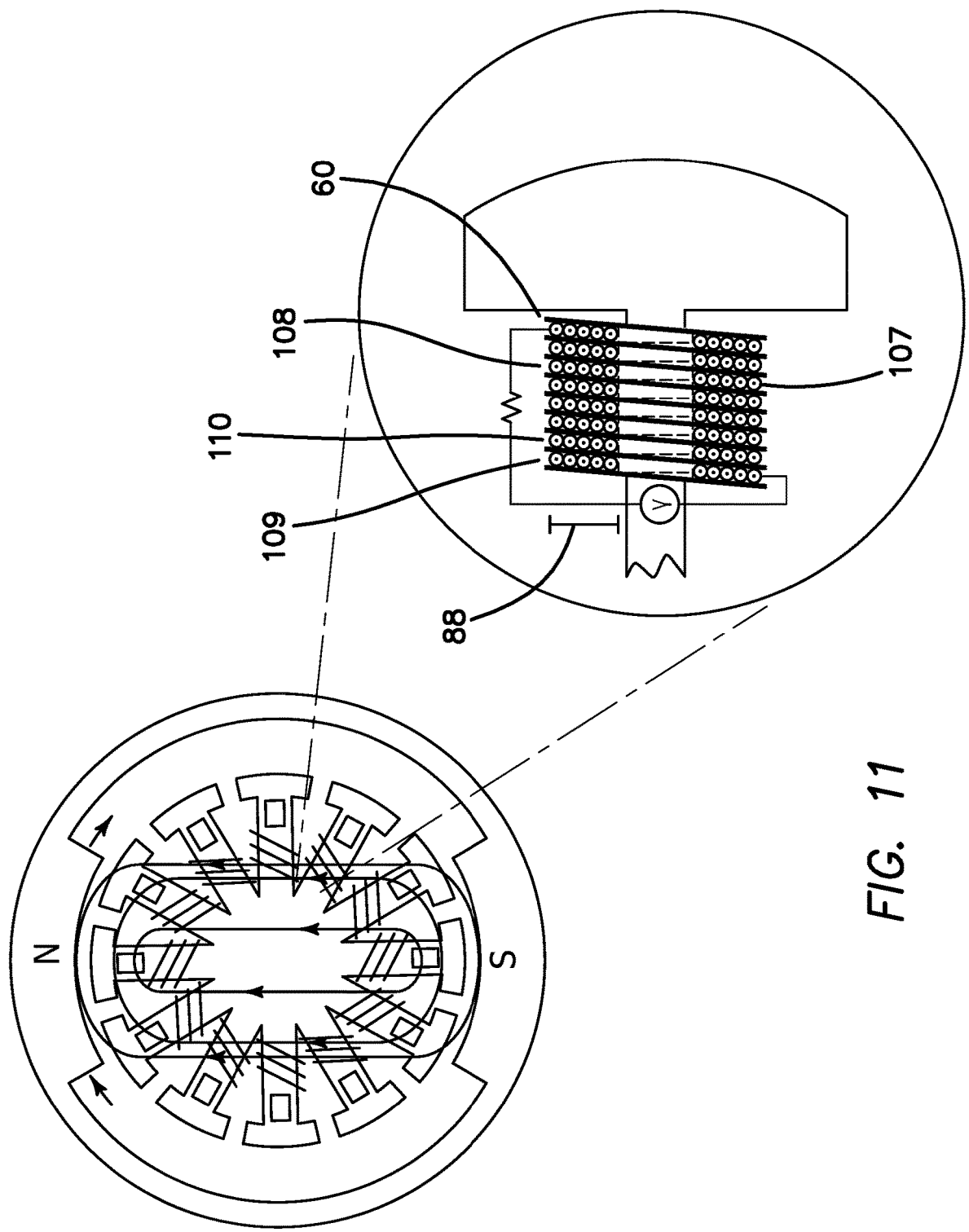
FIG. 11 illustrates the novel solenoid/capacitor technology applied on the winding of an electric motor/generator, according to example embodiments.

FIG. 11 illustrates the novel solenoid/capacitor technology applied on the winding of an electric motor/generator.

FIG. 11 shows the winding of any electric motor using the spiraling loops technology as explained in FIGS. 9 and 10. So, as an additional embodiment of this novel winding technology it is important to mention that spiraled plaque as well as spiraled wire may be employed on any winding where induction technology is needed.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 12 illustrates an example computer system/server node 600, which may represent or be integrated in any of the above-described components, etc.

Figure 12:
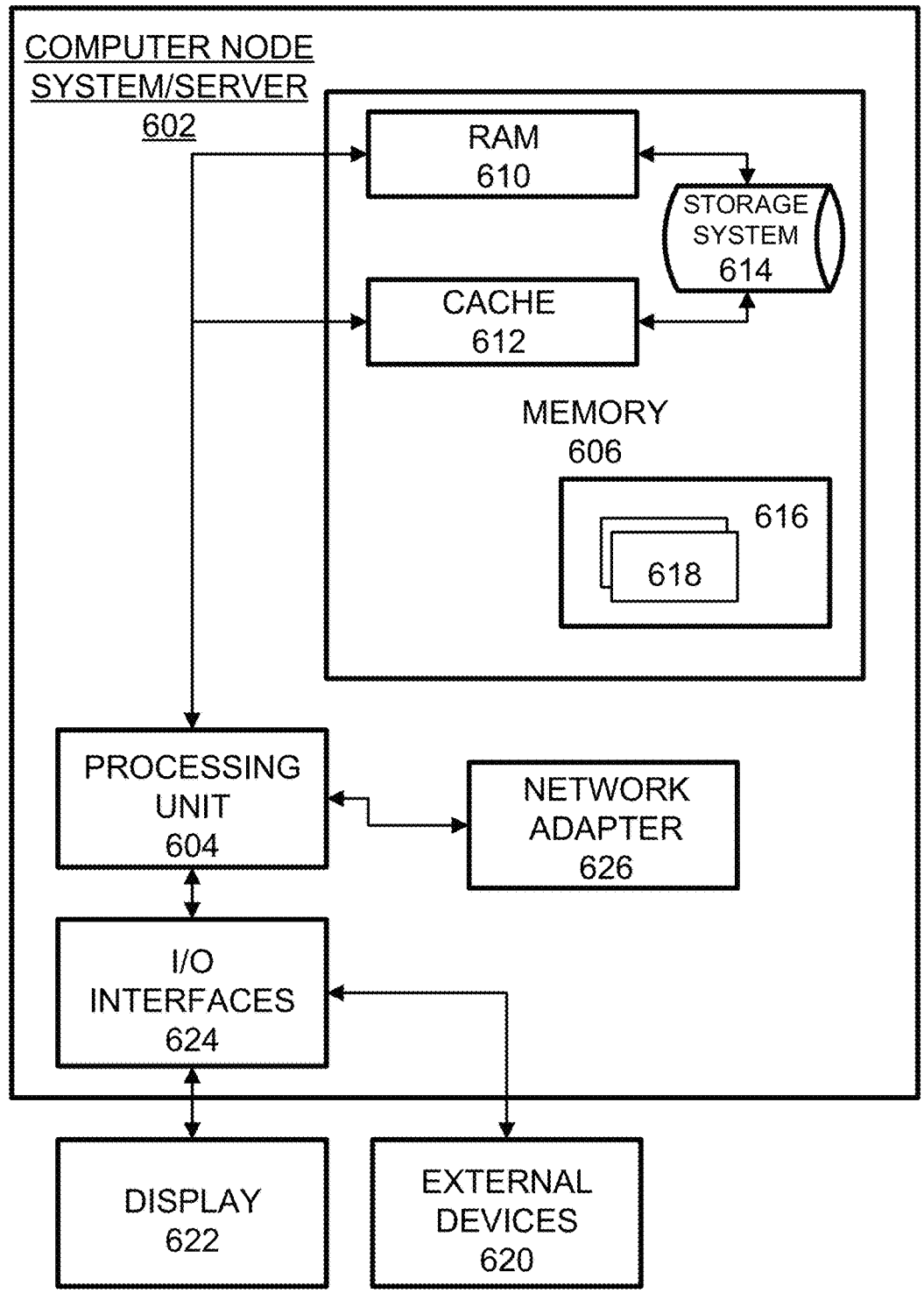
FIG. 12 illustrates an example computer node system that supports one or more of the example embodiments.

FIG. 12 is not intended to suggest any limitation as to the scope of use or functionality of embodiments of the application described herein. Regardless, the computing node 600 is capable of being implemented and/or performing any of the functionality set forth hereinabove.

In the computing node 600 there is a computer system/server 602, which is operational with numerous other general purposes or special purpose computing system environments or configurations. Examples of well-known computing systems, environments, and/or configurations that may be suitable for use with computer system/server 602 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 602 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 602 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 12, the computer system/server 602 may be used in cloud computing node 600 shown in the form of a general-purpose computing device. The components of the computer system/server 602 may include, but are not limited to, one or more processors or processing units 604, a system memory 606, and a bus that couples various system components including system memory 606 to processor 604.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The exemplary computer system/server 602 typically includes a variety of computer system readable media. Such media may be any available media that is accessible by the computer system/server 602, and it includes both volatile and non-volatile media, removable and non-removable media. System memory 606, in one embodiment, implements the flow diagrams of the other figures. The system memory 606 can include computer system readable media in the form of volatile memory, such as random-access memory (RAM) 610 and/or cache memory 612. The computer system/server 602 may further include other removable/non-removable, volatile/non-volatile computer system storage media. By way of example only, storage system 614 can be provided for reading from and writing to a non-removable, non-volatile magnetic media (not shown and typically called a "hard drive"). Although not shown, a magnetic disk drive for reading from and writing to a removable, non-volatile magnetic disk, and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 606 may include at least one program product having a set (e.g., at least one) of program modules that are configured to carry out the functions of various embodiments of the application.

Program/utility 616, having a set (at least one) of program modules 618, may be stored in memory 606 by way of example, and not limitation, as well as an operating system, one or more application programs, other program modules, and program data. Each of the operating system, one or more application programs, other program modules, and program data or some combination thereof, may include an implementation of a networking environment. Program modules 618 generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

The computer system/server 602 may also communicate with one or more external devices 620 such as a keyboard, a pointing device, a display 622, etc.; one or more devices that enable a user to interact with computer system/server 602; and/or any devices (e.g., network card, modem, etc.) that enable computer system/server 602 to communicate with one or more other computing devices. Such communication can occur via I/O interfaces 624. Still yet, the computer system/server 602 can communicate with one or more networks such as a local area network (LAN), a general wide area network (WAN), and/or a public network (e.g., the Internet) via network adapter 626. As depicted, network adapter 626 communicates with the other components of computer system/server 602 via a bus. It should be understood that although not shown, other hardware and/or software components could be used in conjunction with computer system/server 602. Examples include, but are not limited to: microcode, device drivers, redundant processing units, external disk drive arrays, RAID systems, tape drives, and data archival storage systems, etc.

Although an exemplary embodiment of at least one of a system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, recipient or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a Smart phone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these example embodiments, it would be apparent to those of skill in the art that certain modifications, variations, and alternative constructions would be apparent.

While example embodiments of the present application have been described, it is to be understood that the embodiments described are illustrative only and the scope of the application is to be defined solely by the appended claims when considered with a full range of equivalents and modifications (e.g., protocols, hardware devices, software platforms, etc.) thereto.

What is claimed is:

1. A system, comprising:
a processor of a computer node operatively connected to a computer-guided robotic arm configured to manipulate a medical instrument attachable to the robotic arm and comprising a laser beam emitter located at a distal end of the medical instrument; a memory on which are stored machine readable instructions that when executed by the processor, cause the processor to:
cause the robotic arm to perform movements comprising extend, retreat or spin;
acquire imaging data of a patient concurrent to the movements of the robotic arm;
and configure emission parameters of the laser beam based on the imaging data;
wherein the emission parameters of the laser beam comprise direction, intensity and duration of the emission of the laser beam configured to destroy pre-defined shape and volume of cellular tissue of a body of a patient.

2. The system of claim 1, wherein the instructions further cause the processor to control pulses of the laser beam and intensity of the pulses.

3. The system of claim 1, wherein the instructions further cause the processor to acquire the imaging data comprising MRI data, CT scan data or ultrasound data.

4. The system of claim 1, wherein the instructions further cause the processor to auto-regulate frequency and intensity of laser shoots based on a temperature sensor data acquired throughout a laser conducting optic fiber.

5. The system of claim 1, wherein the instructions further cause the processor to acquire real-time data from a plurality of feedback sensors and from at least one infrared camera for positioning of the robotic arm.

6. The system of claim 5, wherein the instructions further cause the processor to coordinate the movements of the robotic arm with movements of other robotic arms using the real-time data from the plurality of feedback sensors and from the at least one infrared camera.

* * * * *